US012600966B2

(12) United States Patent
Rozet et al.

(10) Patent No.: US 12,600,966 B2
(45) Date of Patent: Apr. 14, 2026

(54) METHODS FOR THE TREATMENT OF RETINAL DYSTROPHIES BY EXON-SKIPPING STRATEGY

(71) Applicants: INSERM (INSTITUT NATIONAL DE LA SANTÉ ET DE LA RECHERCHE MÉDICALE), Paris (FR); FONDATION ASILE DES AVEUGLES, Lausanne (CH); UNIVERSITÉ DE PARIS, Paris (FR); ASSISTANCE PUBLIQUE—HÔPITAUX DE PARIS, Paris (FR); FONDATION IMAGINE, Paris (FR)

(72) Inventors: Jean-Michel Rozet, Paris (FR); Xavier Gerard, Lausanne (CH); Iris Barny, Paris (FR); Isabelle Perrault, Paris (FR); Josseline Kaplan, Paris (FR)

(73) Assignees: INSERM (INSTITUT NATIONAL DE LA SANTE ET DE LA RECHERCHE MEDICALE), Paris (FR); FONDATION ASILE DES AVEUGLES, Lausanne (CH); UNIVERSITÉ DE PARIS, Paris (FR); ASSISTANCE PUBLIQUE—HÔPITAUX DE PARIS, Paris (FR); FONDATION IMAGINE, Paris (FR)

( * ) Notice: Subject to any disclaimer, the term of this patent is extended or adjusted under 35 U.S.C. 154(b) by 1148 days.

(21) Appl. No.: 17/606,574

(22) PCT Filed: Apr. 24, 2020

(86) PCT No.: PCT/EP2020/061450
§ 371 (c)(1),
(2) Date: Oct. 26, 2021

(87) PCT Pub. No.: WO2020/216895
PCT Pub. Date: Oct. 29, 2020

(65) Prior Publication Data
US 2022/0340901 A1 Oct. 27, 2022

(30) Foreign Application Priority Data
Apr. 26, 2019 (EP) .................................... 19305541

(51) Int. Cl.
*C12N 15/113* (2010.01)
*C12Q 1/68* (2018.01)

(52) U.S. Cl.
CPC ........ *C12N 15/113* (2013.01); *C12N 2310/11* (2013.01); *C12N 2320/33* (2013.01)

(58) Field of Classification Search
None
See application file for complete search history.

(56) References Cited

U.S. PATENT DOCUMENTS

2019/0037583 A2 *  1/2019  Rozet ...................... A61P 25/00
2022/0098584 A1 *  3/2022  Swildens ........... A61K 31/7125

FOREIGN PATENT DOCUMENTS

WO      2015/004133 A1      1/2015
WO      2016/034680 A2      3/2016
WO      2016/135334 A1      9/2016

OTHER PUBLICATIONS

Barny et al: "AON-Mediated Exon Skipping to Bypass Protein Truncation in Retinal Dystrophies Due to the Recurrent CEP290 C.4723A > T Mutation. Fact or Fiction?", Genes, vol. 10, No. 5, p. 368, May 14, 2019.

(Continued)

*Primary Examiner* — Sean Mcgarry
(74) *Attorney, Agent, or Firm* — WCF IP

(57) ABSTRACT

The invention relates to the skipping of the CEP290 exon 36 in an individual suffering from a retinal dystrophy accounted for by a nonsense mutation or a premature termination codon generated by a frameshift mutation in exon 36 or an upstream exon, including the c.4723A>T, c.4771C>T, c.4714G>T, c.4786_4790del, c.4791_4794del, c.4732G>T, c.4625_4626insCATG (35), c.4792_4795del, c.4801C>T, c.4805C>T, or c.4811G>A mutations, to bypass protein truncation and lessen retinal damages. Here, studying fibroblasts from control individuals, and two patients carrying the CEP290 c.4723A>T nonsense mutation, they show low levels of spontaneous skipping of exon 36 arising from both endogenous basal skipping and mutation-induced skipping. The minimally shortened and mutation-free CEP290 mRNA produced by skipping of exon 36 in the fibroblasts of the two patients is translated into a protein isoform that localizes at the centrosome and allows the formation of primary cilia, yet with elongated axonemes. Using an AON consisting of a sequence set forth as SEQ ID NO: 1, complementary to a nucleic acid sequence of CEP290 pre-mRNA, wherein said AON targeting an mRNA encoding the donor splice site (H36D) is capable to alter splicing by blocking the recognition of exon 36 and bypass protein truncation while maintaining the open reading frame, leading to the production of near full-length CEP290 protein, they were able to increase the abundance of the alternatively spliced mRNA and shortened protein and to reduce axonemal length in patient cells.

Figure 1:
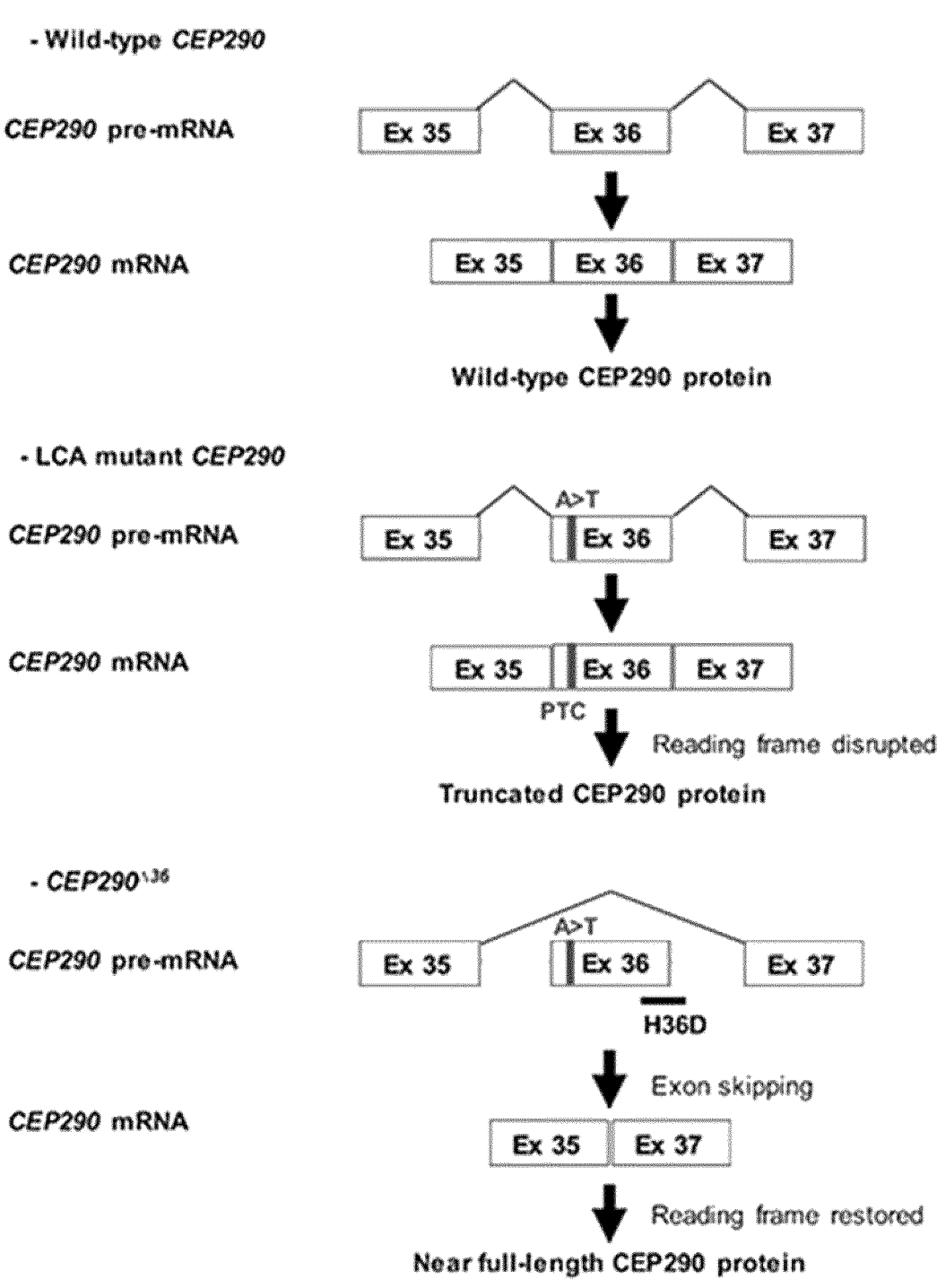

22 Claims, 12 Drawing Sheets
Specification includes a Sequence Listing.

(56) References Cited

OTHER PUBLICATIONS

Parfitt et al: "Identification and Correction of Mechanisms Underlying Inherited Blindness in Human iPSC-Derived Optic Cups", Cell Stem Cell, vol. 18, No. 6, pp. 769-781, Apr. 14, 2016.
Roosing et al: "A Rare Form of Retinal Dystrophy Caused by Hypomorphic Nonsense Mutations in CIP290", Genes, vol. 8, No. 8, p. 208, Aug. 22, 2017.

* cited by examiner

A

B

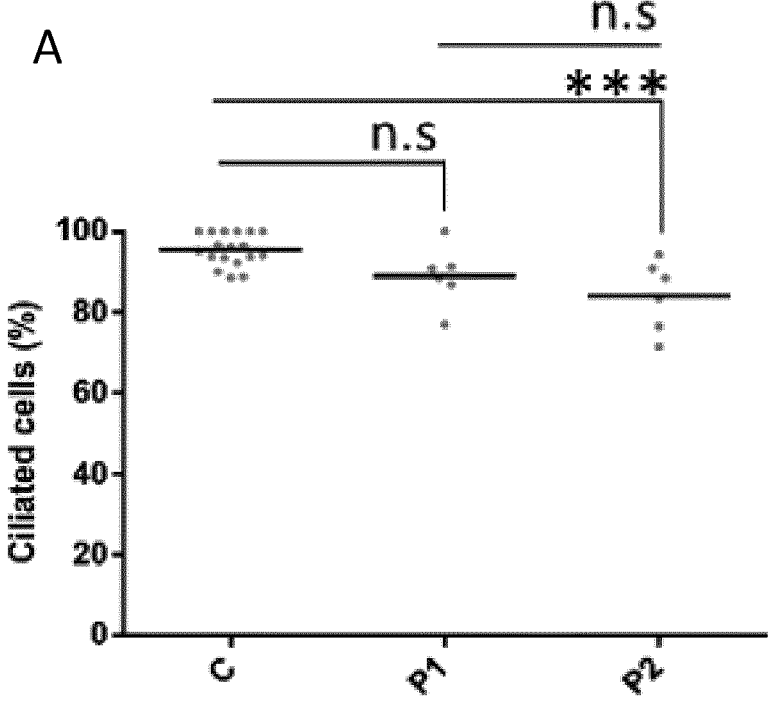
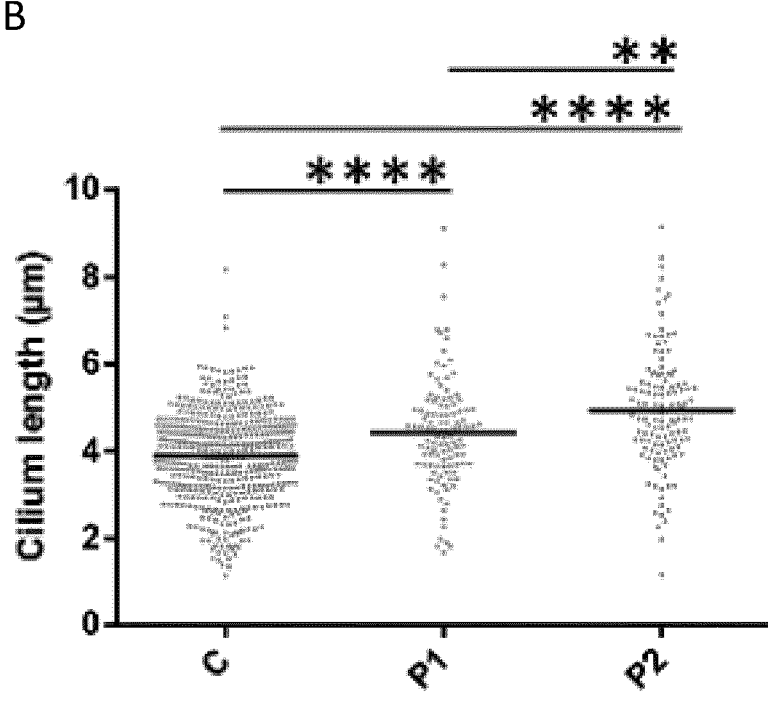
Figure 6A-B

C

A

B

A

D
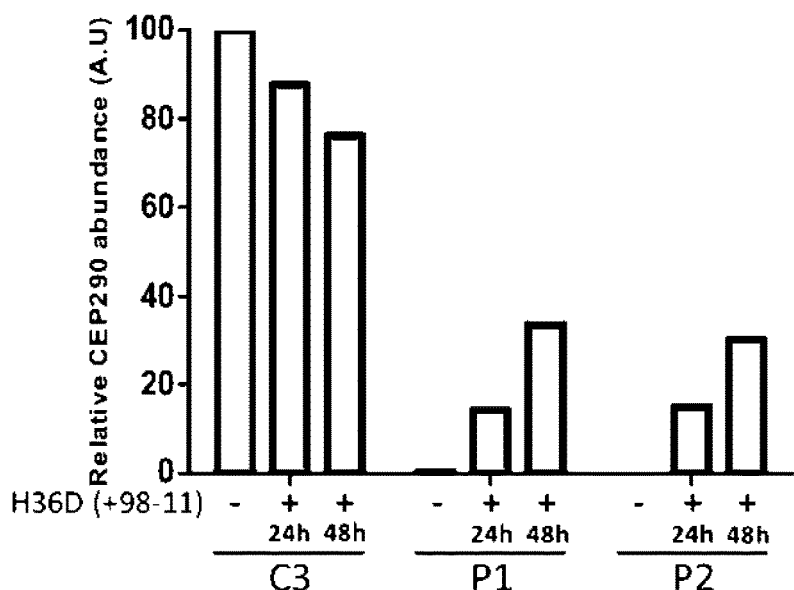
Figure 8D
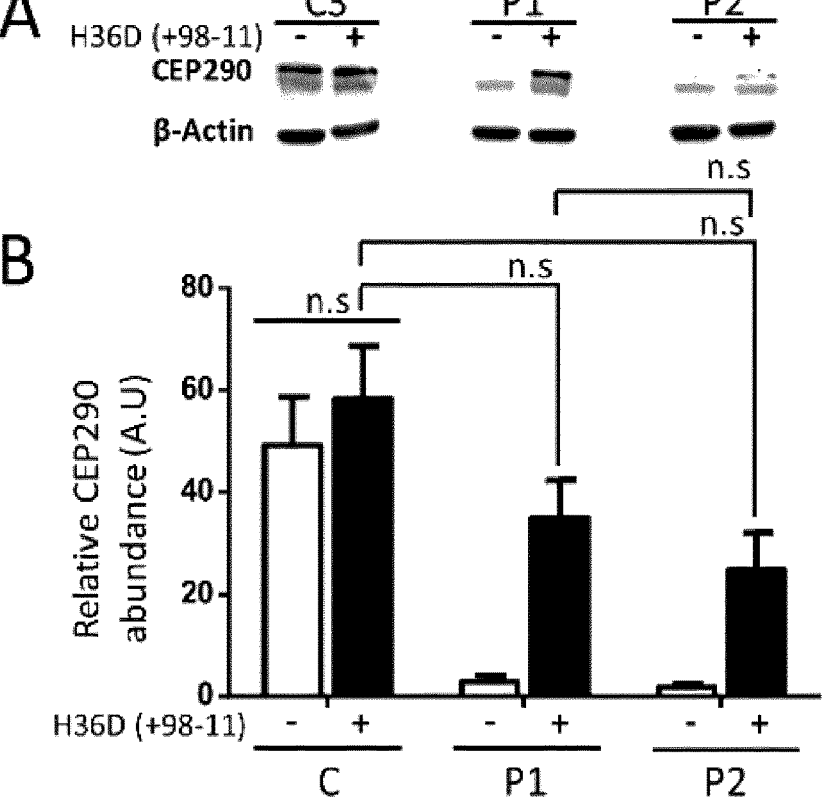
Figure 9A-B

C

D

METHODS FOR THE TREATMENT OF RETINAL DYSTROPHIES BY EXON-SKIPPING STRATEGY

FIELD OF THE INVENTION

The invention is in the field of gene therapy, particularly exon skipping strategy is used to treat retinal dystrophies.

BACKGROUND OF THE INVENTION

Leber congenital amaurosis (LCA, MIM204000) is a group of neonatal-onset and severe retinal dystrophies and a leading cause of incurable blindness in childhood (Frequency 1:30 000; 20% of children attending schools for the Blind in Western Europe) [1]. It typically occurs as a non-syndromic disease that displays large genetic, allelic and physio-pathological heterogeneity, challenging therapeutic developments [2]. Mutations in CEP290 (MIM610142) encoding a widely expressed centrosomal protein involved in cilia formation and maintenance [3], are the leading cause of the disease, referred to as LCA type 10 (LCA10; MIM611755) [4,5]. Despite early-onset visual loss, LCA10 individuals display prolonged (>30 years) sparing of central photoreceptors with intact visual brain pathway, creating the conditions to develop therapies built on correcting genetic lesions [6]. A large number of LCA10-causing mutations are reported, including the highly prevalent c.2991+1655A>G (p.Cys998*) and c.4723A>T (p.Lys1575*) variants involved in 10% and 2.5% of all LCA cases, respectively [5,7]. The c.2991+1655A>G change activates a deep intronic cryptic splice site and introduces a frameshifting pseudo-exon in the mRNA [8-11]. Antisense oligonucleotides (AONs) have proven effective to redirect the splicing machinery towards the consensus splice sites and bypass protein truncation in primary fibroblasts, IPSC-derived 3D retinal organoids and humanized mice carrying the mutation [8,10,12]. Subsequently, a phase II/III clinical trial (NCT03140969) has been launched which demonstrated safety and clinical relevance (vision improvement) of intravitreal injections of splice-modulating oligonucleotide (sepofarsen) [11]. The phase II/III trial is an ongoing (PQ-110-003, NCT03913143; multiple dose, double-masked, randomized, sham-controlled clinical trial of sepofarsen in patients). The c.4723A>T variant, like the vast majority of other LCA10 mutations, is predicted to truncate the protein and is amenable to gene augmentation therapy. However, this approach is challenging due to both the CEP290 cDNA size (7.4 Kb) which over-exceed cargo capacities of AAV vectors (<5 Kb) preferred in the field of retinal diseases [13-15] and the risk of overexpression toxicity [16,17]. Interestingly, consistent with an important role in cilia metabolism, CEP290 mutations have been associated with additional human phenotypes, including oculo-renal Senior Loken syndrome (SLSN6, MIM610189), oculo-cerebro-renal Joubert syndrome (JBTSS, MIM610188) and embryo-lethal Meckel syndrome type 4 (MKS4; MIM611134)[18]. Observation of endogenous basal exon-skipping producing low-levels of alternatively spliced coding CEP290 mRNAs has inspired a model of pathogenesis according to which disease severity is a function of the amount of CEP290 a cell can produce from mutant alleles [19]. Consistently, low levels of PTC-free CEP290 mRNA produced by endogenous basal alternative splicing and/or nonsense-associated altered splicing have been identified in fibroblasts from individuals with biallelic CEP290 truncating mutations but mild retinal phenotypes [20-22]. Lessening the disease through somatic frame-restoration mechanisms is reminiscent of genetic reversion in dystrophin-positive muscular fibers from individuals with Duchene muscular dystrophy which inspired AON-mediated exon skipping to bypass dystrophin truncation and switch the disease to attenuated Becker muscular dystrophy.

SUMMARY OF THE INVENTION

The invention relates to an antisense oligonucleotide consisting of a sequence complementary to a nucleic acid sequence of CEP290 gene, wherein said antisense oligonucleotide targeting the donor splice site of exon 36 (H36D) has the following sequence: SEQ ID NO:1 and is capable to alter splicing by blocking the recognition of exon 36 by spliceosome and allows bypassing protein truncation associated with any mutation introducing a premature termination codon in exon 36, while maintaining the reading frame, and leads to the production of near full-length CEP290 protein. In particular, the present invention is defined by the claims.

DETAILED DESCRIPTION OF THE INVENTION

In an attempt to better understand the relationship between CEP290 and retinal dystrophies such as Leber congenital amaurosis (LCA), inventors have worked on different regions of the CEP290 gene and have worked on the c.4723A>T mutation in the exon 36 of the CEP290 gene. Particularly, this mutation results in the apparition of a premature termination codon in the portion of the CEP290 mRNA encoded by exon 36, resulting in the degradation of mutant mRNAs by the nonsense-mediated mRNA decay (NMD) and/or leading to the translation of unfunctional truncated proteins.

Inventors have used an antisense oligonucleotide for hiding consensus splice sites (donor and acceptor splice sites) from the spliceosome (splicing machinery). This antisense oligonucleotide is complementary to a sequence comprising the donor splice site. They considered AON-mediated skipping of CEP290 exon 36 to bypass protein truncation resulting from any CEP290 mutation, the consequence of which is the introduction of a premature termination codon in exon 36. More particularly, from at least one CEP290 mutation selected from the group consisting of: c.4723A>T, c.4771C>T, c.4714G>T, c.4786_4790del, c.4791_4794del, c.4732G>T, c.4625_4626insCATG (35), c.4792_4795del, c.4801C>T, c.4805C>T, or c.4811G>A. Here, studying fibroblasts from control individuals, they showed that exon 36 undergoes low-level of endogenous skipping, producing very low levels of minimally shortened CEP290 mRNA and protein that preserves the wild-type centrosomal localization. Studying fibroblasts from two unrelated individuals homozygous for the c.4723A>T mutation, they showed that the skipping of exon 36 is more prominent than in controls due to a combination of endogenous and mutation-induced skipping. The minimally shortened and mutation-free CEP290 mRNA produced by skipping of exon 36 is translated into a protein isoform that localizes at the centrosome and allows the formation of primary cilia, yet with elongated axonemes compared to control counterparts. Using AON specific to the donor consensus splice-site of exon 36 in patient and control fibroblasts, they were able to increase the abundance of the alternatively spliced mRNA and shortened protein and to reduce axonemal length in patient cells.

Using AON specific to the donor consensus splice-site of exon 36 in patient and control fibroblasts, they were able to increase the abundance of the alternatively spliced mRNA and shortened protein and to reduce axonemal length in patient cells.

The inventors have shown that the administration of AON induces the skipping of the exon 36, maintaining an open reading frame and allowing the production of a minimally shortened CEP290 protein which is surprisingly functional.

In the present invention, the inventors report data supporting the feasibility of an antisense oligonucleotide-mediated exon skipping strategy to bypass protein truncation resulting from mutations introducing a premature termination codon in exon 36 and lessen the retinal damages. The invention thus provides use of such exon-skipping strategy for the treatment of retinal dystrophies.

An Antisense Oligonucleotide Consisting of a Sequence Complementary to a Nucleic Acid Sequence of CEP290 Gene In a first aspect, the invention relates to an antisense oligonucleotide consisting of a sequence complementary to a nucleic acid sequence of CEP290 gene, wherein said antisense oligonucleotide, targeting the donor splice site of exon 36 (H36D) has the following sequence: SEQ ID NO:1 and is capable to alter splicing by blocking the recognition of exon 36 by splicing machinery and allows bypassing protein truncation associated with any mutation introducing a premature termination codon in exon 36, while maintaining the reading frame, and lead to the production of near full-length CEP290 protein.

In a particular embodiment, the CEP290 is a CEP290 pre-mRNA.

In a particular embodiment, the antisense oligonucleotide according to the invention targets the donor splice site of exon 36 of the CEP290 gene and allows bypassing any truncating mutation in this exon by removing the exon from the mature mRNA.

In a further embodiment, the antisense oligonucleotide according to the invention, wherein, the exon 36 of the CEP290 gene has at least one mutation selected from the group consisting of: c.4723A>T, c.4732G>T, c.4771C>T, c.4714G>T, c.4786_4790del, c.4791_4794del, c.4732G>T, c.4714G>T, c.4625_4626insCATG (35), c.4792_4795del, c.4801C>T, c.4805C>T, or c.4811G>A.

As used herein, the term "CEP290" has its general meaning in the art and refers to a protein encoded by the CEP290 gene. CEP290 is an integral component of the ciliary gate that bridges the transition zone between the cilia and cytoplasm. The protein plays an important role in maintaining the structural integrity of this gate, and thus has a crucial role in maintaining ciliary function (Craige, B et al. The Journal of Cell Biology. 190, 927-40 (2010).). The term may include naturally occurring "CEP290" and variants and modified forms thereof. The CEP290 can be from any source, but typically is a mammalian (e.g., human and non-human primate) CEP290, particularly a human CEP290. An exemplary native human CEP290 amino acid sequence is provided in GenPept database under accession number [EAW97414.1] and an exemplary native human nucleotide sequence encoding for CEP290 is provided in GenBank database under accession number [NM_025114.3].

The term "antisense oligonucleotide" or AON refers to a single strand of DNA, RNA, or modified nucleic acids that is complementary to a chosen sequence. Antisense RNA can be used to modulate splicing or prevent protein translation of certain mRNA strands by binding to them. Antisense DNA can be used to target a specific, complementary (coding or non-coding) RNA. In a particular embodiment, the antisense oligonucleotide is an antisense RNA. In another embodiment, the antisense oligonucleotide is an antisense DNA.

Oligonucleotides are designed to complement suitable sequences, usually RNA sequences within the pre-mRNA molecule which are required for correct splicing of the targeted exon, thereby blocking splicing reactions that would incorporate the targeted exon into mature mRNA or excluding mutant exon without disrupting the reading frame. An AON typically binds to the sequence which it complements and sterically hinders the splicing reaction. Sequences are selected so as to be specific, i.e. the AONs are complementary only to the sequences of the pre-mRNA and not to other nucleic acid sequences. The AONs used in the practice of the invention may be of any suitable type, e.g. oligodeoxyribonucleotides, oligoribonucleotides, morpholinos, tricyclo-DNA-antisense oligonucleotides, U7- or U1-mediated AONs or conjugate products thereof such as peptide-conjugated or nanoparticle-complexed AONs. AONs employed in the practice of the invention are generally from about 10 to 50 nucleotides in length, and may be for example, about 10 or fewer, or about 15, or about 20 or about 30 nucleotides or more in length. The optimal length of the AONs for a targeted complementary sequence is generally in the range of from about 15 to about 30 nucleotides long depending on the chemical backbone used and on the target sequence. Typically, morpholino-AONs are about 25 nucleotides long, 2'PMO-AONs are about 20 nucleotides long, and tricyclo-AONs are about 15 nucleotides long.

The AONs of the invention can be synthesized de novo using any of a number of procedures well known in the art. For example, the b-cyanoethyl phosphoramidite method (Beaucage et al., 1981); nucleoside H-phosphonate method (Garegg et al., 1986; Froehler et al., 1986, Garegg et al., 1986, Gaffney et al., 1988). These chemistries can be performed by a variety of automated nucleic acid synthesizers available in the market. These nucleic acids may be referred to as synthetic nucleic acids. Alternatively, AONs can be produced on a large scale in plasmids (see Sambrook, et al., 1989). AONs can be prepared from existing nucleic acid sequences using known techniques, such as those employing restriction enzymes, exonucleases or endonucleases. AONs prepared in this manner may be referred to as isolated nucleic acids.

The AONs may be or are stabilized. A "stabilized" AON refers to an AON that is relatively resistant to in vivo degradation (e.g. via an exo- or endo-nuclease). Stabilization can be a function of length or secondary structure. Alternatively, AON stabilization can be accomplished via phosphate backbone modifications. Preferred stabilized AONs of the instant invention have a modified backbone, e.g. have phosphorothioate linkages to provide maximal activity and protect the AON from degradation by intracellular exo- and endo-nucleases. Other possible stabilizing modifications include phosphodiester modifications, combinations of phosphodiester and phosphorothioate modifications, methylphosphonate, methylphosphorothioate, phosphorodithioate, p-ethoxy, and combinations thereof. Chemically stabilized, modified versions of the AONs also include "Morpholinos" (phosphorodiamidate morpholino oligomers, PMOs), 2'-O-Met oligomers, 2'-Fluoro (2'-F) oligomers, tricyclo (tc)-DNAs, U7 short nuclear (sn) RNAs, tricyclo-DNA-oligoantisense molecules (U.S. Provisional Patent Application Ser. No. 61/212,384 For: Tricyclo-DNA Antisense Oligonucleotides, Compositions and Methods for the Treatment of Disease, filed Apr. 10, 2009, the complete contents of which is hereby incorporated by reference), unlocked nucleic acid (UNA), peptide nucleic acid (PNA), serinol nucleic acid (SNA), twisted intercalating nucleic acid (TINA), anhydrohexitol nucleic acid (HNA), cyclohexenyl nucleic acid (CeNA), D-altritol nucleic acid (ANA) and morpholino nucleic acid (MNA) have also been investigated in splice modulation. Recently, nucleobase-modified AOs containing 2-thioribothymidine, and 5-(phenyltriazol)-2-de-oxyuridine nucleotides have been reported to induce exon skipping (Chen S, Le B T, Chakravarthy M, Kosbar T R, Veedu R N. Systematic evaluation of 2'-Fluoro modified chimeric antisense oligonucleotide-mediated exon skipping in vitro. Sci Rep. 2019 Apr. 15; 9(1):6078.)

In a particular embodiment, the antisense oligonucleotides of the invention may be 2'-O-Me RNA/ENA chimera oligonucleotides (Takagi M, Yagi M, Ishibashi K, Take-shima Y, Surono A, Matsuo M, Koizumi M.Design of 2'-O-Me RNA/ENA chimera oligonucleotides to induce exon skipping in dystrophin pre-mRNA. Nucleic Acids Symp Ser (Oxf). 2004; (48):297-8).

Other forms of AONs that may be used to this effect are AON sequences coupled to small nuclear RNA molecules such as U1 or U7 in combination with a viral transfer method based on, but not limited to, lentivirus or adeno-associated virus (Denti, M A, et al, 2008; Goyenvalle, A, et al, 2004).

In another particular embodiment, the antisense oligo-nucleotides of the invention are 2'-O-methyl-phosphoroth-ioate nucleotides.

In a particular embodiment, the antisense oligonucleotide of the invention is complementary to a sequence comprising the donor splice site (H36D) with at least one mutation selected from the group consisting of: c.4723A>T, c.4771C>T, c.4714G>T, c.4786_4790del, c.4791_4794del, c.4732G>T, c.4625_4626insCATG (35), c.4792_4795del, c.4801C>T, c.4805C>T, or c.4811G>A.

In a particular embodiment, the antisense oligonucleotide, complementary to a nucleic acid sequence of CEP290 exon 36, that is necessary for skipping the exon 36 inserted into the mutant CEP290 mRNA.

In a particular embodiment, the antisense oligonucleotide of the present invention, comprising a nucleic acid sequence SEQ ID NO:1.

In a more particular embodiment, the antisense oligonucleotide of the present invention, consisting of a nucleic acid sequence SEQ ID NO:1.

In a particular embodiment, the antisense oligonucleotide of the invention is complementary to a nucleic acid sequence that is necessary for enhancing the splicing of the exon 36 of CEP290 mRNA which contains a premature termination codon resulting from a mutation in exon 36 or a frameshift mutation in exon 36 or an upstream exon that introduces a premature termination codon in exon 36.

In a particular embodiment, the antisense oligonucleotide of the invention is complementary to a nucleic acid sequence that is necessary for enhancing the splicing of the exon 36 of CEP290 mRNA which contains at least one mutation selected from the group consisting of: c.4723A>T, c.4771C>T, c.4714G>T, c.4786_4790del, c.4791_4794del, c.4732G>T, c.4625_4626insCATG (35), c.4792_4795del, c.4801C>T, c.4805C>T, or c.4811G>A.

In further embodiment, the antisense oligonucleotide of the invention is complementary to a nucleic acid sequence that is necessary for enhancing the splicing of the exon 36 of CEP290 mRNA which contains a nonsense mutation such as c.4723A>T.

As used herein, the term "complementary" includes "fully complementary" and "substantially complementary", mean-ing there will usually be a degree of complementarity between the oligonucleotide and its corresponding target sequence of more than 80%, preferably more than 85%, still more preferably more than 90%, most preferably more than 95%. For example, for an oligonucleotide of 20 nucleotides in length with one mismatch between its sequence and its target sequence, the degree of complementarity is 95%. In particular, the invention relates to an antisense oligonucle-otide complementary to a nucleic acid sequence of CEP290 exon 36 that is necessary for skipping exon 36 inserted into the mutants mRNA having at least 25% sequence identity with target sequence.

According to the invention, a first amino acid sequence having at least 25% of identity with a second amino acid sequence means that the first amino acid sequence has 25%; 26%; 27%; 28%; 29%; 30%; 31%; 32%; 33%; 34%; 35%; 36%; 37%; 38%; 39%; 40%; 41%; 42%; 43%; 44%; 45%; 46%; 47%; 48%; 49%; 50%; 51%; 52%; 53%; 54%; 55%; 56%; 57%; 58%; 59%; 60%; 61%; 62%; 63%; 64%; 65%; 66%; 67%; 68%; 69%; 70%; 71%; 72%; 73%; 74%; 75%; 76%; 77%; 78%; 79%; 80%; 81%; 82%; 83%; 84%; 85%; 86%; 87%; 88%; 89%; 90%; 91%; 92%; 93%; 94%; 95%; 96%; 97%; 98%; 99% or 100% of identity with the second amino acid sequence. Sequence identity is frequently mea-sured in terms of percentage identity (or similarity or homology); the higher the percentage, the more similar are the two sequences. Methods of alignment of sequences for comparison are well known in the art. Various programs and alignment algorithms are described in: Smith and Waterman, Adv. Appl. Math., 2:482, 1981; Needleman and Wunsch, J. Mol. Biol., 48:443, 1970; Pearson and Lipman, Proc. Natl. Acad. Sci. U.S.A., 85:2444, 1988; Higgins and Sharp, Gene, 73:237-244, 1988; Higgins and Sharp, CABIOS, 5:151-153, 1989; Corpet et al. Nuc. Acids Res., 16:10881-10890, 1988; Huang et al., Comp. Appls Biosci., 8:155-165, 1992; and Pearson et al., Meth. Mol. Biol., 24:307-31, 1994). Altschul et al., Nat. Genet., 6:119-129, 1994, presents a detailed consideration of sequence alignment methods and homology calculations. By way of example, the alignment tools ALIGN (Myers and Miller, CABIOS 4:11-17, 1989) or LFASTA (Pearson and Lipman, 1988) may be used to perform sequence comparisons (Internet Program® 1996, W. R. Pearson and the University of Virginia, fasta20u63 version 2.0u63, release date December 1996). ALIGN com-pares entire sequences against one another, while LFASTA compares regions of local similarity. These alignment tools and their respective tutorials are available on the Internet at the NCSA Website, for instance. Alternatively, for compari-sons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., J. Mol. Biol., 215:403-410, 1990; Gish. & States, Nature Genet., 3:266-272, 1993; Madden et al. Meth. Enzymol., 266:131-141, 1996; Altschul et al., Nucleic Acids Res., 25:3389-3402, 1997; and Zhang & Madden, Genome Res., 7:649-656, 1997.

In some embodiments, the antisense oligonucleotides according to the invention comprise a sequence complementary to a nucleic acid sequence of CEP290 exon 36 that is necessary for skipping exon 36 inserted into the mutants CEP290 mRNA. In some embodiments, the antisense oligonucleotides according to the invention comprise a sequence complementary to a nucleic acid sequence of CEP290 exon 36 that is necessary for skipping exon 36 inserted into the mutants CEP290 mRNA, wherein said antisense oligonucleotides comprises the sequence set forth as SEQ ID NO:1.

A combination of said antisense oligonucleotides may also be used according to the invention to modulate the splicing of the exon 36 of CEP290 mRNA which contains at least one mutation.

In a particular embodiment, the antisense oligonucleotide according to the invention is capable of inducing exon-skipping and consists in a sequence complementary to a nucleic acid sequence of CEP290 gene that is necessary for modulate the splicing of the exon 36 of CEP290 which contains at least one mutation.

In a particular embodiment, the antisense oligonucleotide comprises a nucleic acid sequence set forth as SEQ ID NO:1.

Typically, said antisense oligonucleotides have a length of at least 15 nucleotides.

In a particular embodiment, the antisense oligonucleotide for the use according to the invention, wherein, said antisense oligonucleotide has a length of at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107 or 108 nucleotides.

TABLE 1

Oligonucleotide sequences containing 2'-O-Methyl RNA bases and full-length phosphorothioate backbones. The H_sense is a sense oligonucleotide and used as control, whereas the H36D (+98 -11) is antisense oligonucleotide (AON) designed to target the donor splice site at the junction of the CEP290 exon 36/ intron 36, and the H36ESE (+63 +84) directed against ESE sequences within CEP290 exon 36.

| Name | Sequences |
|---|---|
| H36D (+98 -11) RNA AON | SEQ ID NO: 1<br>5'-uagaaucuuacccaagccguuu-3' |
| H_sense RNA | SEQ ID NO : 2<br>5'-acuacaggcugauaguucacua-3' |
| H36D(+98 -11) DNA | SEQ ID NO: 3<br>5'-tagaatcttacccaagccgttt-3' |
| H_sense DNA | SEQ ID NO : 4<br>5'-actacaggctgatagttcacta-3' |
| H36ESE (+63 +84) RNA AON | SEQ ID NO : 5<br>5'-uagugaacuaucagccuguagu-3' |
| H36ESE (+63 +84) DNA | SEQ ID NO : 6<br>5'-tagtgaactatcagcctgtagt-3' |

Within introns, a donor site (5' end of the intron), a branch site (near the 3' end of the intron) and an acceptor site (3' end of the intron) are required for splicing. The donor splice site includes an almost invariant sequence GU at the 5' end of the intron, within a larger, less highly conserved region. The acceptor splice site at the 3' end of the intron terminates the intron with an almost invariant AG sequence.

In a particular embodiment, the invention relates to an antisense oligonucleotide for hiding splicing regulatory motifs (ESE sequences). In particular embodiment, said antisense oligonucleotides comprise a sequence set forth as SEQ ID NO:5 (H36ESE). In particular embodiment, said antisense oligonucleotides consist of a sequence set forth as SEQ ID NO:5 (H36ESE).

In some embodiments, the antisense oligonucleotides according to the invention comprise a sequence set forth as SEQ ID NO: 5, complementary to a nucleic acid sequence of CEP290 exon 36 that is necessary for skipping exon 36 inserted into the mutants CEP290 mRNA.

The antisense oligonucleotides are used as splice-switching oligonucleotides (SSO) to bypass protein truncation resulting from a mutation on exon 36 CEP290. Typically, the administration of SSO designed to skip exon 36 allows bypassing the mutation by allowing the production of minimally shortened mRNA with an open reading frame and the production of a minimally shortened CEP290 protein which is functional. Splice-switching oligonucleotides direct pre-mRNA splicing by binding sequence elements and blocking access to the transcript by the spliceosome and other splicing factors. In the context of the invention, inventors have used data bases (http://mfold.rna.albany.edu/ and http://rulai-.cshl.edu/cgi-bin/tools/ESE3/esefinder.cgi) to identify a targetable sequence in the CEP290 pre-mRNA around the donor-splice site of exon 36.

In particular embodiment, the inventors have used data bases to identify a targetable sequence in the CEP290 pre-mRNA around the site of H36ESE and/or H36D.

Typically said method is called exon skipping strategy.

As used herein, the term "exon" refers to a defined section of nucleic acid that encodes for a protein, or a nucleic acid sequence that is represented in the mature form of an RNA molecule after either portions of a pre-processed (or precursor) RNA have been removed by splicing. The mature RNA molecule can be a messenger RNA (mRNA) or a functional form of a non-coding RNA, such as rRNA or tRNA.

As used herein, the term "exon skipping" generally refers to the process by which an entire exon, or a portion thereof, is removed from a given pre-processed RNA, and is thereby excluded from being present in the mature RNA, such as the mature mRNA that is translated into a protein. In the context of the invention, the exon skipping is used to bypass (hide) a mutation in exon 36 from the spliceosome machinery and to increase the abundance of the alternatively spliced mRNA and shortened protein and to reduce axonemal length. Thus, this strategy allows to obtain a short CEP290 protein which is functional. Thus, this strategy prevents the apparition of premature termination codon in the exon 36.

Hence, the portion of the protein that is otherwise encoded by the skipped exon is not present in the expressed form of the protein, typically creating an altered, though still functional, form of the protein. In certain embodiments, the exon being skipped is a mutant exon naturally existing in the human CEP290 gene, which may contain a mutation or other alteration in its sequence that otherwise causes a premature stop codon which leads to form a truncated CEP290 protein.

As used herein, the terms "preventing the apparition of premature termination codon of the exon 36", "blocking the recognition of exon 36" or "removing a premature termination codon in the exon 36" refer to the removal of said exon in mature mRNA by a modification of splicing using the exon skipping strategy (see FIG. 1). The invention thus provides methods for obtaining a functional protein using exon skipping technology. The method involves blocking or preventing the incorporation into mature mRNA of targeted exon 36 which encodes amino acids sequences that are responsible for the protein dysfunction. The AONs bind to complementary required sequences in the pre-mRNA and cause modification of splicing. Hence, the targeted exon is not included in the mature mRNA that is translated into protein, and the amino acid sequences encoded by the targeted exon are missing from the translated protein. Thus, a near full-length CEP290 protein, a short functional protein is obtained by carried out the exon skipping strategy.

Thus, the strategy of exon skipping restores the function and/or the stability of CEP290 protein in the range of at least about 10%, preferably about 20%, 30%, 40%, 50%, 60%, 70%, 80%, 90% or even 100%, compared to a protein translated from a mutated CEP290. Such restoration of the protein may be observed on a micro level. For example, the restoration of protein expression and/or localisation is evaluated by immunohistochemistry, immunofluorescence, Western-blot analyses; restoration/amelioration of protein functionality evaluated by the improvement of cilia assembly and/or maintenance, restoration/amelioration of cone functionality . . . or on a macro level (i.e. amelioration/restoration of clinical symptoms such as visual acuity).

Those skilled in the art will recognize that there are many ways to determine or measure a level of functionality of a protein, and to determine a level of increase or decrease of functionality e.g. in response to a treatment protocol. Such methods include but are not limited to measuring or detecting an activity of the protein, etc. Such measurements are generally made in comparison to a standard or control or "normal" sample. In addition, when the protein's lack of functionality is involved in a disease process, disease symptoms may be monitored and/or measured in order to indirectly detect the presence or absence of a correctly functioning protein, or to gauge the success of a treatment protocol intended to remedy the lack of functioning of the protein. Particularly, the functionality of CEP290 can be measured by several methods recognized in the art. Generally, the removal of the exon 36 which contains a premature termination codon resulting from a mutation in exon 36 or a frameshift mutation in exon 36 or an upstream exon. In a particular embodiment, the removal of the exon 36 which contains at least one mutation is carried out by using at least one antisense oligonucleotide (AON).

In a particular embodiment, the antisense oligonucleotides of the invention may be delivered in vivo alone or in association with a vector.

In its broadest sense, a "vector" is any vehicle capable of facilitating the transfer of the antisense oligonucleotide of the invention to the cells. Preferably, the vector transports the nucleic acid to cells with reduced degradation relative to the extent of degradation that would result in the absence of the vector. In general, the vectors useful in the invention include, but are not limited to, naked plasmids, non-viral delivery systems (electroporation, sonoporation, cationic transfection agents, liposomes, nanoparticules, etc. . . . ), phagemids, viruses, other vehicles derived from viral or bacterial sources that have been manipulated by the insertion or incorporation of the antisense oligonucleotide nucleic acid sequences. Viral vectors are a preferred type of vector and include, but are not limited to nucleic acid sequences from the following viruses: RNA viruses such as a retrovirus (as for example moloney murine leukemia virus and lentiviral derived vectors), harvey murine sarcoma virus, murine mammary tumor virus, and rous sarcoma virus; adenovirus, adeno-associated virus; SV40-type viruses; polyoma viruses; Epstein-Barr viruses; papilloma viruses; herpes virus; vaccinia virus; polio virus. One can readily employ other vectors not named but known to the art.

Typically, viral vectors according to the invention include adenoviruses and adeno-associated (AAV) viruses, which are DNA viruses that have already been approved for human use in gene therapy. Currently, 12 different AAV serotypes (AAV1 to 12) are known, each with different tissue tropisms (Wu, Z Mol Ther 2006; 14:316-27). Recombinant AAV are derived from the dependent parvovirus AAV (Choi, V W J Virol 2005; 79:6801-07). The adeno-associated virus type 1 to 12 can be engineered to be replication deficient and is capable of infecting a wide range of cell types and species (Wu, Z Mol Ther 2006; 14:316-27). It further has advantages such as, heat and lipid solvent stability; high transduction frequencies in cells of diverse lineages, including hemopoietic cells; and lack of superinfection inhibition thus allowing multiple series of transductions. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those skilled in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by, intranasal sprays or drops, rectal suppository and orally. Preferably, said DNA plasmid is injected through an intraocular way (intravitreal, sub retinal, suprachoroidal . . . ). It may also be administered into the epidermis or a mucosal surface using a gene-gun. The plasmids may be given in an aqueous solution, dried onto gold particles or in association with another DNA delivery system including but not limited to liposomes, dendrimers, cochleate and micro-encapsulation. In a particular embodiment, the antisense oligonucleotide nucleic acid sequence is under the control of a heterologous regulatory region, e.g., a heterologous promoter. The promoter can also be, e.g., a viral promoter, such as CMV promoter or any synthetic promoters.

Use of Antisense Oligonucleotides of the Invention

In a second aspect, the invention relates to a method for performing antisense oligonucleotide-mediated exon skipping in a subject in need, thereof comprising the step of delivering to target cells of the subject an amount of an antisense oligonucleotide, wherein the subject suffers from a retinal dystrophy caused by a mutation which modifies the splicing and/or creates a premature termination codon by a nonsense mutation in exon 36 or a frameshift mutation in exon 36 or an upstream exon in a gene important to the functioning and/or the survival of the target cells, wherein said nucleic acid sequence of CEP290 gene is selected from the group consisting of the ESE sequences of said exon 36 and a sequence comprising the donor splice site around the exon 36/intron 36 boundary and wherein the antisense oligonucleotide performs antisense oligonucleotide-mediated exon skipping in the pre-mRNA from the gene which mutation causes the retinal dystrophies in the target cells of the subject.

In a particular embodiment, the method for performing antisense oligonucleotide-mediated exon skipping according to the invention, wherein the subject suffers from a retinal dystrophies caused by at least one mutation selected from the group consisting of: c.4723A>T, c.4771C>T, c.4714G>T, c.4786_4790del, c.4791_4794del, c.4732G>T, c.4625_4626insCATG (35), c.4792_4795del, c.4801C>T, c.4805C>T, or c.4811G>A, which modify the splicing and introduce a premature termination codon in exon 36 in a gene important to the functioning and/or the survival of the target cells, wherein said nucleic acid sequence of CEP290 gene is selected from the group consisting of the ESE sequences of said exon 36 and a sequence comprising the donor or acceptor splice sites (around the exon 36/intron 36 boundary) and wherein the antisense oligonucleotide performs antisense oligonucleotide-mediated exon skipping in the pre-mRNA from the gene which mutation causes the retinal dystrophies in the target cells of the subject.

As used herein, the term "target cells" in a subject are one or more of the following non-limiting types of ciliated cells, eye cells, including photoreceptors, cone cells, rod cells, retinal epithelial cells, retinal bipolar cells, retinal ganglion cells, RPE cells, horizontal cells, amacrine cells and Müller cells.

Mutations in CEP290 (MIM610142) encoding a widely expressed centrosomal protein involved in cilia formation and maintenance [3] but also in cell division (Valente, E. M.; Silhavy, J. L.; Brancati, F.; Barrano, G.; Krishnaswami, S. R.; Castori, M.; Lancaster, M. A.; Boltshauser, E.; Boccone, L.; Al-Gazali, L.; et al. Mutations in CEP290, which encodes a centrosomal protein, cause pleiotropic forms of Joubert syndrome. Nat. Genet. 2006, 38, 623-625.), are the leading cause of the disease, referred to as LCA type 10.

Accordingly, in a particular embodiment, the target cells are ciliated cells. As used herein, the term "ciliated" herein encompasses the vibratile/motile cilia, primary cilia or the flagella expressed by cells.

In the eye, the retina is the tissue that covers the wall of the eye bottom. Retinal tissue is composed by three cell layers, including the photoreceptor cell layer. A photoreceptor is divided in two parts: an inner and outer segment linked together through a connecting cilium. This primary cilium is an essential structure to transport proteins from the inner segment, where they are synthesized, to the outer segment, where phototransduction takes place. The protein encoded by the CEP290 gene is localized at the base of the connecting cilium. An altered function induces abnormalities in intracellular trafficking, leads to ciliary structure defects and/or results in absence or shortened outer segment within photoreceptor cells.

As used herein, the term "retinal dystrophies" refers to chronic and progressive disorders in which the anatomy and/or function of the retina are altered. Retina is located at the back of the eye near the optic nerve and is made up of millions of light-sensitive cells called 'photoreceptors'. The purpose of the retina is to receive light that the lens has focused, convert the light into neural signals, and send these signals on to the brain for visual recognition. When damage to the photoreceptor cells occur, the retina is unable to function properly and struggles to process and transmit sight information to the brain.

In a particular embodiment, the method according to the invention wherein, the retinal dystrophies are selected from the group consisting of Leber congenital amaurosis and other early-onset severe retinal dystrophies (LCA-like), rod-cone dystrophies (retinitis pigmentosa), cone-rod dystrophies, macular dystrophies including age-related macular degeneration, any ciliopathy involving the retina including Joubert syndrome, Senior-Loken syndrome, Bardet-Biedel syndrome, Meckel and Meckel-like syndromes, Refsum syndrome, Stargardt disease, Usher syndrome, hereditary optic neuropathies, congenital stationary night blindness, dyschromatopsia and achromatopsia.

In a particular embodiment, the method according to the invention, wherein the retinal dystrophy is Leber congenital amaurosis (LCA). The term "Leber congenital amaurosis (LCA)" is a common cause of blindness in childhood (10%). It is the most severe inherited retinal dystrophy, responsible for blindness or profound visual deficiency at birth or in the first months of life. It can present as an early-onset severe rod-cone or an early-onset severe cone-rod dystrophy.

In a particular embodiment, the method according to the invention, wherein the antisense oligonucleotide is selected from the group consisting of oligodeoxyribonucleotides, oligoribonucleotides, Locked Nucleic Acid (LNA) oligonucleotides, morpholinos oligonucleotides, tricyclo-DNA-antisense oligonucleotides, U7- or U1-mediated antisense oligonucleotides, peptide-conjugated, nanoparticle-complexed antisense oligonucleotides, 2'-O-Me RNA/ENA chimera oligonucleotides, and 2'-O-methyl-phosphorothioate oligonucleotides.

In a third aspect, the invention relates to an antisense oligonucleotide consisting of a sequence complementary to a nucleic acid sequence of the CEP290 gene that is necessary to alter splicing and exclude the exon encoding the premature termination codon inserted into the CEP290 mRNA by a nonsense mutation in exon 36 or a frameshift mutation in exon 36 or an upstream exon, wherein said nucleic acid sequence of CEP290 gene is a sequence comprising the ESE motifs and wherein said sequence is selected from the group consisting of the exon splicing enhancer (ESE) sequences of said mutant exon and a sequence comprising the donor splice site for use for restoring the function of CEP290 in a cell carrying a nonsense mutation present in the exon 36 of the CEP290 gene, or a frameshift mutation in exon 36 or an upstream exon that introduces a premature termination codon in exon 36, in a subject harbouring said mutation.

In another word, the invention relates to an antisense oligonucleotide consisting of a sequence complementary to a nucleic acid sequence of CEP290 gene that is necessary to alter splicing and exclude the exon encoding the premature termination codon inserted into the CEP290 mRNA by a nonsense mutation in exon 36 or a frameshift mutation in exon 36 or an upstream exon, wherein said nucleic acid sequence of CEP290 gene is a sequence comprising the ESE motifs and wherein said sequence is selected from the group consisting of the exon splicing enhancer (ESE) sequences of said mutant exon and a sequence comprising the donor splice site mutation suitable for restoring the function of CEP290 in a cell carrying a nonsense mutation present in the exon 36 of the CEP290 gene, or a frameshift mutation in exon 36 or an upstream exon that introduces a premature termination codon in exon 36, in a subject harbouring said mutation.

In a particular embodiment, the antisense oligonucleotide according to the invention targets the splice donor site (H36D).

In a particular embodiment, the antisense oligonucleotide for use according to the invention, wherein the premature termination codon inserted into the exon 36 is due to at least one mutant selected from the group consisting of: c.4723A>T, c.4771C>T, c.4714G>T, c.4786_4790del, c.4791_4794del, c.4732G>T, c.4625_4626insCATG (35), c.4792_4795del, c.4801C>T, c.4805C>T, or c.4811G>A of CEP290 mRNA, wherein said nucleic acid sequence of CEP290 gene is a sequence comprising the ESE motifs and wherein said sequence is selected from the group consisting of the exon splicing enhancer (ESE) sequences of said mutant exon and a sequence comprising the donor splice site for use for restoring the function of CEP290 in a cell carrying at least one mutation selected from the group consisting of: c.4723A>T, c.4771C>T, c.4714G>T, c.4786_4790del, c.4791_4794del, c.4732G>T, c.4625_4626insCATG (35), c.4792_4795del, c.4801C>T, c.4805C>T, or c.4811G>A present in the CEP290 gene in a subject harbouring said mutation.

In a particular embodiment, the antisense oligonucleotide complementary to a nucleic acid sequence of CEP290 gene for the use according to the invention, wherein said cell carrying a nonsense mutation present in the exon 36, or a frameshift mutation in exon 36 or an upstream exon that introduces a premature termination codon in exon 36, present in the CEP290 gene is a ciliated cell.

In a particular embodiment, the antisense oligonucleotide complementary to a nucleic acid sequence of CEP290 gene for the use according to the invention, wherein said cell carrying at least one mutation selected from the group consisting of: c.4723A>T, c.4771C>T, c.4714G>T, c.4786_4790del, c.4791_4794del, c.4732G>T, c.4625_4626insCATG (35), c.4792_4795del, c.4801C>T, c.4805C>T, or c.4811G>A present in the CEP290 gene is a ciliated cell.

In a particular embodiment, the antisense oligonucleotide complementary to a nucleic acid sequence of CEP290 gene for the use according to the invention, wherein the antisense oligonucleotide consisting of a nucleic acid sequence SEQ ID NO:1

In a particular embodiment, the antisense oligonucleotide complementary to a nucleic acid sequence of CEP290 gene for the use according to the invention, wherein, said antisense oligonucleotide has a length of at least 15 nucleotides.

In a particular embodiment, the antisense oligonucleotide complementary to a nucleic acid sequence of CEP290 gene for the use according to the invention, wherein, said antisense oligonucleotide has a length of at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107 or 108 nucleotides.

In a particular embodiment, the antisense oligonucleotide complementary to a nucleic acid sequence of CEP290 gene for the use according to the invention, is administered intravitreally to a subject harbouring at least one mutation selected from the group consisting of: c.4723A>T, c.4771C>T, c.4714G>T, c.4786_4790del, c.4791_4794del, c.4732G>T, c.4625_4626insCATG (35), c.4792_4795del, c.4801C>T, c.4805C>T, or c.4811G>A.

In a fourth aspect, the invention relates to a method of treating retinal dystrophies in a subject harbouring a nonsense mutation, located in the exon 36 of CEP290 gene or a frameshift mutation in exon 36 or an upstream exon resulting in the apparition of a premature termination codon in exon 36, leading to a truncated protein, wherein said method comprises the step of modulating the splicing of the exon 36 which contains a nonsense mutation or a premature termination codon generated by a frameshift mutation within the same or an upstream exon wherein said method is carried out by exposing the pre-mRNA that includes exon 36 encoding the protein CEP290 to an antisense oligonucleotide (AON) which is complementary to the sequence of mutant exon harbouring premature termination codon.

In a particular embodiment, the method of treating retinal dystrophies according to the present invention comprising the step of modulating the splicing of the exon 36 which contains at least one mutation which leads to a truncated protein, wherein said method is carried out by exposing the pre-mRNA that includes exon 36 encoding the protein CEP290 to at least one antisense oligonucleotide (AON) according to the invention.

In a particular embodiment, the invention relates to a method of treating retinal dystrophies in a subject harbouring at least one mutation selected from the group consisting of: c.4723A>T, c.4771C>T, c.4714G>T, c.4786_4790del, c.4791_4794del, c.4732G>T, c.4625_4626insCATG (35), c.4792_4795del, c.4801C>T, c.4805C>T, or c.4811G>A, located in the exon 36 of CEP290 gene resulting in the apparition of a premature termination codon leading to a truncated protein, wherein said method comprises the step of modulating the splicing of the exon 36 which contains at least one mutation selected from the group consisting of: c.4723A>T, c.4771C>T, c.4714G>T, c.4786_4790del, c.4791_4794del, c.4732G>T, c.4625_4626insCATG (35), c.4792_4795del, c.4801C>T, c.4805C>T, or c.4811G>A, wherein said method is carried out by exposing the pre-mRNA that includes exon 36 encoding the protein CEP290 to an antisense oligonucleotide (AON) which is complementary to the sequence of mutant exon harbouring premature termination codon.

In a particular embodiment, the method according to the invention, wherein a therapeutically effective amount of the AON according to the invention is administered to a subject harbouring a nonsense mutation in exon 36, including the c.4723A>T mutation, or a premature termination codon in exon 36 generated by a frameshift mutation within the same or an upstream exon.

In a particular embodiment, the method according to the invention, wherein a therapeutically effective amount of the AON according to the invention is administered to a subject harbouring at least one mutation selected from the group consisting of: c.4723A>T, c.4771C>T, c.4714G>T, c.4786_4790del, c.4791_4794del, c.4732G>T, c.4625_4626insCATG (35), c.4792_4795del, c.4801C>T, c.4805C>T, or c.4811G>A.

In a particular embodiment, the method according to the invention wherein, the antisense oligonucleotide is complementary to a sequence comprising the donor splice site or acceptor splice site as described above.

In a particular embodiment, the method according to the invention, wherein the antisense oligonucleotide comprises a nucleic acid sequence set forth as SEQ ID NO: 1.

In a particular embodiment, the method according to the invention, wherein the antisense oligonucleotide consisting of a nucleic acid sequence set forth as SEQ ID NO: 1.

As used herein, the terms "treating" or "treatment" refer to both prophylactic or preventive treatment as well as curative or disease modifying treatment, including treatment of subject at risk of contracting the disease or suspected to have contracted the disease as well as subject who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

As used herein, the term "subject", refers to any mammals, such as a rodent, a feline, a canine, and a primate. Particularly, in the present invention, the subject is a human afflicted with or susceptible to be afflicted with by the mutation in CEP290 exon 36. In a particular embodiment, the subject is a human afflicted or susceptible to be afflicted by a nonsense mutation in exon 36, including the c.4723A>T mutation, or a premature termination codon in exon 36 generated by a frameshift mutation within the same or an upstream exon of the CEP290 gene. In another embodiment, the subject is a human afflicted or susceptible to be afflicted by at least one mutation selected from the group consisting of: c.4723A>T, c.4771C>T, c.4714G>T, c.4786_4790del, c.4791_4794del, c.4732G>T, c.4625_4626insCATG (35), c.4792_4795del, c.4801C>T, c.4805C>T, or c.4811G>A in exon 36 of CEP290. In a particular embodiment, the subject is a human afflicted or susceptible to be afflicted with retinal dystrophies. More particularly, the subject afflicted or susceptible to be afflicted with LCA.

As used herein the terms "administering" or "administration" refer to the act of injecting or otherwise physically delivering a substance as it exists outside the body (e.g., the AON of the invention alone or with vectors) into the subject, more particularly into vitreous, aqueous humour, ciliary body tissue(s) or cells and/or extra-ocular muscles, retina (e.g. after retinal detachment) or even in the suprachoridal space. Electroporation or sonoporation means may also be suitable for delivering the antisense oligonucleotides of the invention (alone or with vectors of the invention). When a disease, or a symptom thereof, is being treated, administration of the substance typically occurs after the onset of the disease or symptoms thereof. When a disease or symptoms thereof, are being prevented, administration of the substance typically occurs before the onset of the disease or symptoms thereof.

In a particular embodiment, the naked AON is administered. In some embodiments, the method according to the invention, wherein AON is delivered intraocularly, intravitreally, subretinally, parenterally, intravenously, intracerebroventricularly, or intrathecally. In particular embodiment, aqueous solutions (naked) are especially suitable for intravenous, intramuscular, intravitreal, subretinal, subcutaneous and intraperitoneal administration.

In a particular embodiment, the antisense oligonucleotides of the invention (naked or with or vectors of the invention) is administered intravitreally to a subject harbouring a nonsense mutation or a premature termination codon in exon 36 generated by a frameshift mutation within the same or an upstream exon mutation in the CEP290 gene.

In a particular embodiment, the antisense oligonucleotides of the invention (naked or with or vectors of the invention) is administered intravitreally to a subject harbouring at least c.4723A>T, c.4771C>T, c.4714G>T, c.4786_4790del, c.4791_4794del, c.4732G>T, c.4625_4626insCATG (35), c.4792_4795del, c.4801C>T, c.4805C>T, or c.4811G>A, mutation in the CEP290 gene.

A "therapeutically effective amount" is intended for a minimal amount of active agent which is necessary to impart therapeutic benefit to a subject. For example, a "therapeutically effective amount" to a subject is such an amount which induces, ameliorates or otherwise causes an improvement in the pathological symptoms, disease progression or physiological conditions associated with or resistance to succumbing to a disorder. It will be understood that the total daily usage of the compounds of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidential with the specific compound employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Pharmaceutical Compositions

In a fifth aspect, the present invention relates to a pharmaceutical composition containing the antisense oligonucleotide of the invention (alone or with a vector of the invention) for use in the treatment of retinal dystrophies in a subject harbouring a nonsense mutation or a premature termination codon in exon 36 generated by a frameshift mutation within the same or an upstream exon mutation in the CEP290 gene.

In a particular embodiment, the pharmaceutical according to the invention (alone or with a vector of the invention) for use in the treatment of retinal dystrophies in a subject harbouring at least one mutation selected from the group consisting of: c.4723A>T, c.4771C>T, c.4714G>T, c.4786_4790del, c.4791_4794del, c.4732G>T, c.4625_4626insCATG (35), c.4792_4795del, c.4801C>T, c.4805C>T, or c.4811G>A.

Pharmaceutical compositions of the present invention may also include a pharmaceutically or physiologically acceptable carrier such as saline, sodium phosphate, etc. The compositions will generally be in the form of a liquid, although this does not need to always be the case. Suitable carriers, excipients and diluents include lactose, dextrose, sucrose, sorbitol, mannitol, starches, gum acacia, calcium phosphates, alginate, tragacanth, gelatin, calcium silicate, microcrystalline cellulose, polyvinylpyrrolidone, cellulose, water syrup, methyl cellulose, methyl and propylhydroxy-benzoates, mineral oil, etc. The formulations can also include lubricating agents, wetting agents, emulsifying agents, preservatives, buffering agents, etc. Those skilled in the art will also recognize that nucleic acids are often delivered in conjunction with lipids (e.g. cationic lipids or neutral lipids, or mixtures of these), frequently in the form of liposomes or other suitable micro- or nano-structured material (e.g. micelles, lipocomplexes, dendrimers, emulsions, cubic phases, nanoparticules, etc.).

Typically, the antisense oligonucleotides of the invention (naked or with vectors of the invention) may be delivered in a pharmaceutically acceptable ophthalmic vehicle, such that the antisense oligonucleotide of the invention (naked or with vectors of the invention) can penetrate the corneal and internal regions of the eye, as for example the anterior chamber, posterior chamber, vitreous body, aqueous humor, vitreous humor, cornea, iris/ciliary, lens, choroid/retina and sclera. The pharmaceutically-acceptable ophthalmic vehicle may, for example, be an ointment, vegetable oil or an encapsulating material.

Alternatively, the antisense oligonucleotides of the invention (naked or with vectors of the invention) may be injected directly into the vitreous, aqueous humour, ciliary body tissue(s) or cells and/or extra-ocular muscles, retina (e.g. after retinal detachment) or even in the suprachoridal space. Electroporation or sonoporation means may also be suitable for delivering the antisense oligonucleotides of the invention (alone or with vectors of the invention).

In a particular embodiment, the pharmaceutical composition containing the antisense oligonucleotide of the invention (naked or with or vectors of the invention) is administered intravitreally to a subject harbouring a nonsense mutation or a premature termination codon in exon 36 generated by a frameshift mutation within the same or an upstream exon mutation in the CEP290 gene.

In a particular embodiment, the pharmaceutical composition containing the antisense oligonucleotide of the invention (naked or with or vectors of the invention) is administered intravitreally to a subject harbouring at least c.4723A>T, c.4771C>T, c.4714G>T, c.4786_4790del, c.4791_4794del, c.4732G>T, c.4625_4626insCATG (35), c.4792_4795del, c.4801C>T, c.4805C>T, or c.4811G>A mutation in the CEP290 gene.

One skilled in the art will recognize that the amount of an AON to be administered will be an amount that is sufficient to induce amelioration of unwanted disease symptoms. Such an amount may vary inter alia depending on such factors as the gender, age, weight, overall physical condition, of the patient, etc. and may be determined on a case by case basis. The amount may also vary according to the type of condition being treated, and the other components of a treatment protocol (e.g. administration of other medicaments such as steroids, etc.).

If a viral-based delivery of AONs is chosen, suitable doses will depend on different factors such as the viral strain that is employed, the route of delivery (intramuscular, intravenous, intra-arterial or other), Those skilled in the art will recognize that such parameters are normally worked out during clinical trials. Even a partial or intermittent relief of symptoms may be of great benefit to the recipient. In addition, treatment of the patient is usually not a single event. Rather, the AONs of the invention will likely be administered on multiple occasions, that may be, depending on the results obtained, several days apart, several weeks apart, or several months apart, or even several years apart. This is especially true for the treatment of Leber congenital amaurosis since the disease is not cured by this treatment, i.e. the gene that encodes the protein will still be defective and the encoded protein will still possess an unwanted, destabilizing feature such as an exposed proteolytic recognition site, unless the AONs of the invention are administered.

The invention will be further illustrated by the following figures and examples. However, these examples and figures should not be interpreted in any way as limiting the scope of the present invention.

FIGURES

FIG. 1: AON-mediated splicing alteration of CEP290 pre-mRNA to bypass protein truncation. An exonic mutation in CEP290 pre-mRNA (c.4723A>T, in red) introduces a premature termination codon (PTC) within exon 36 to CEP290 mRNA. Administration of AON (in black), targeting the splice donor site (H36D), is predicted to alter splicing by blocking the recognition of exon 36. Exclusion of exon 36 (CEP290Δ36) should allow bypassing protein truncation while maintaining the reading frame, and lead to the production of near full-length CEP290 protein.

FIG. 2: Naturally occurring exclusion of CEP290 exon 36 encompassing premature stop codon. (A) Relative expression of WT (gray bar) and mutant (black bars) full-length isoforms, and (B) skipped (CEP290Δ36; hatched bars) CEP290 mRNAs in control (C1-C3) and patient (P1 and P2) fibroblasts as determined by RT-qPCR using GUSB and RPLP0 genes as reference. C corresponds to C1, C2 and C3 pooled values. Values are the mean±SEM derived from ten independent experiments. ****$p \leq 0.0001$, n.s=not significant.

Figure 3:
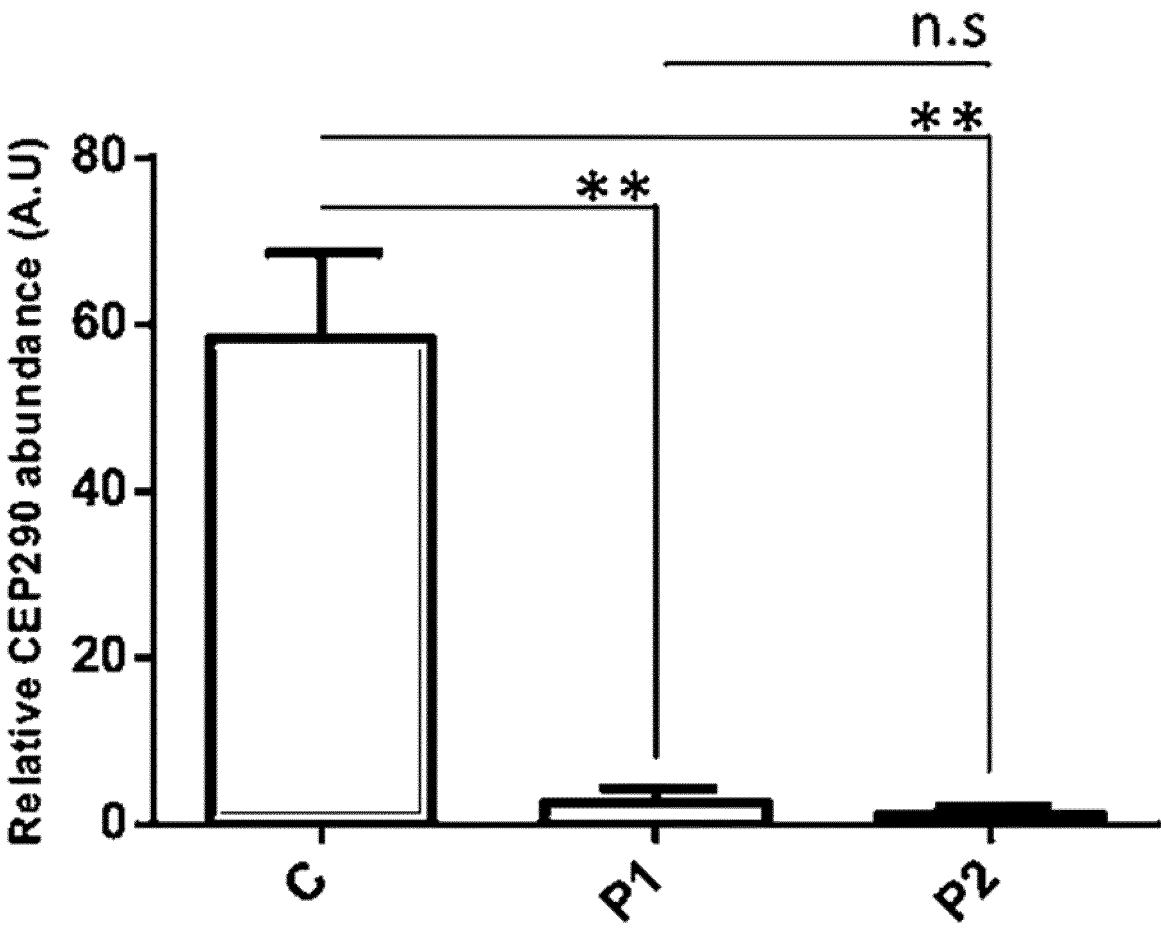

FIG. 3: Effect of the natural exclusion of PTC-encoding exon 36 on CEP290 protein production. Immunodetection of the CEP290 protein in control cell lines (C1-C3) and mutant fibroblasts (P1 and P2). β-Actin was used for normalization. Quantification of CEP290 protein abundance. C corresponds to C1, C2 and C3 pooled values. Values were determined by computed-densitometry analysis of CEP290 and β-actin expression in each sample and are the mean±SEM derived from four independent experiments. **$p \leq 0.01$, n.s=not significant.

Figure 4:
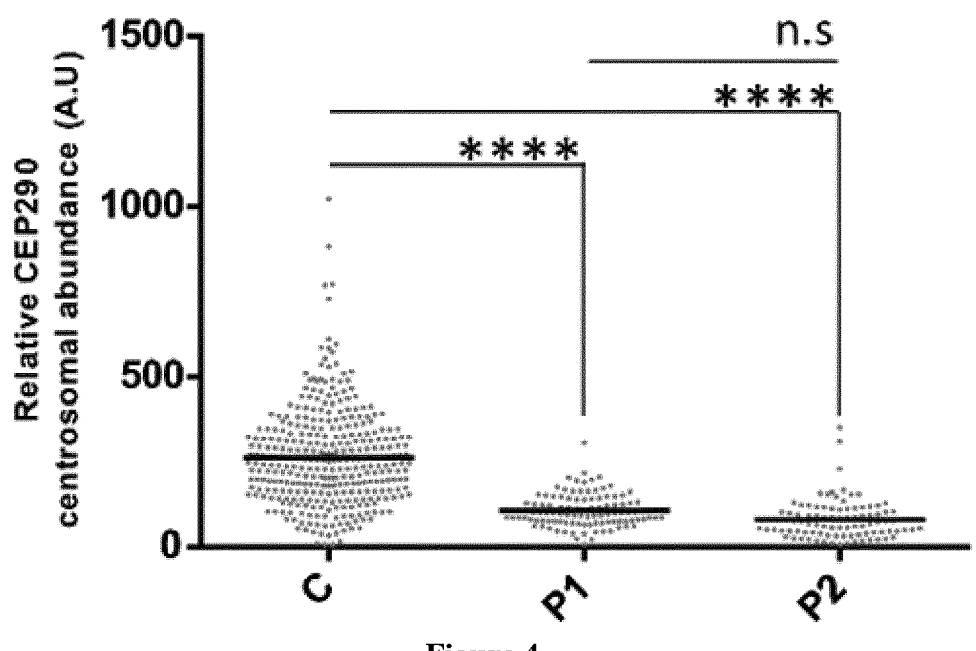

FIG. 4: CEP290 expression assessment in quiescent cells. Quantification of the CEP290 immunofluorescence intensity at the basal body in each cell line (C represents the pooled values of C1, C2 and C3). Each dot depicts the labeling intensity of the protein in individual cells from six microscope fields (recorded automatically). The solid line indicates the mean. ****$p \leq 0.0001$, n.s=not significant. A.U.=arbitrary unit.

Figure 5:
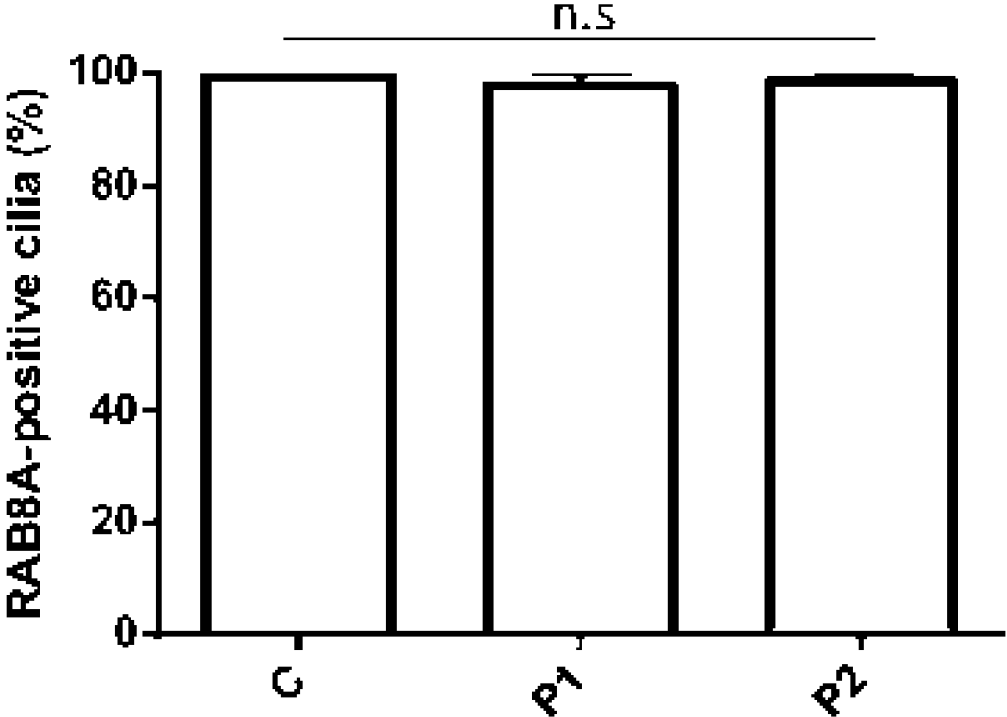
Figure 5:
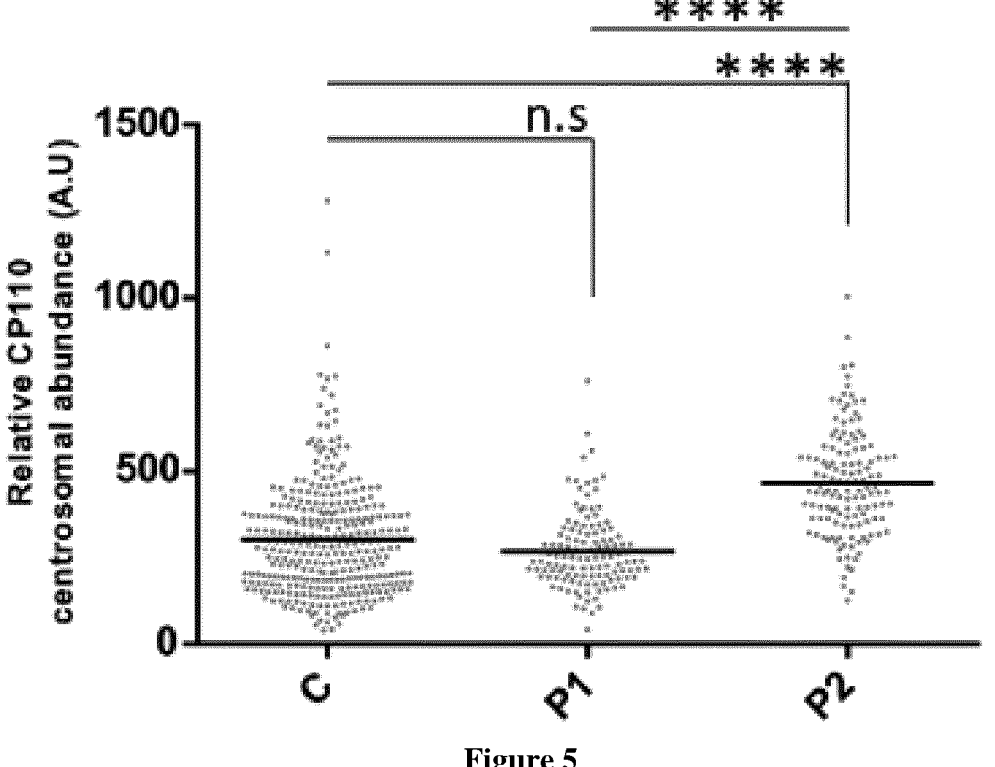

FIG. 5: Localization and abundance of CEP290 centriolar satellite partners. Quantification of RAB8A-positive cilia. Values are the mean±SEM ($n \geq 50$ cilia for each group). Quantification of CP110 immunofluorescence intensity at centrosomes in quiescent fibroblasts. Values are the mean±SEM Immunolabeling was performed from 90-100% confluent cells. All automatic intensity measures were recorded from 6 fields. C corresponds to C1, C2 and C3 pooled values. ****$p \leq 0.0001$, n.s=not significant. A.U.=arbitrary unit.

FIG. 6. Ciliogenesis and axonemal trafficking. (A) Percentage of ciliated cells and (B) length of cilia axonemes in control and patient fibroblasts. A minimum of 90 ciliated cells were considered for each cell lines. (C) Quantification of IFT88-positive cilia. Bars represent the mean±SEM ($n \geq 80$ cilia for each group). C regroups the values of C1, C2 and C3. $p \leq 0.01$, *$p \leq 0.001$, ****$p \leq 0.0001$, n.s=not significant.

Figure 7A:
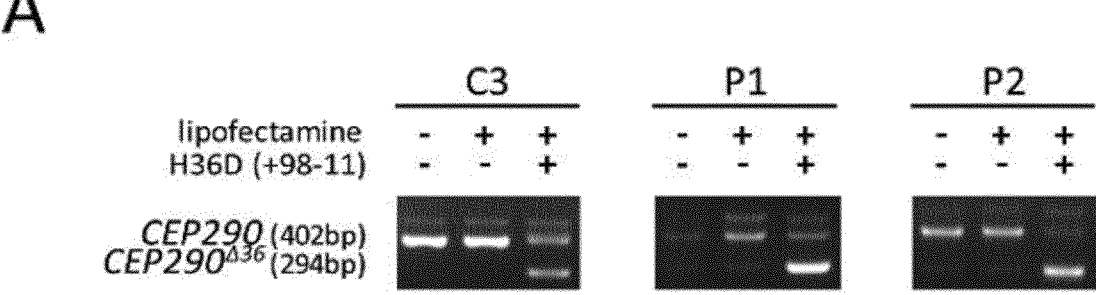

FIG. 7: Effect of AON-mediated exon 36 skipping on CEP290 mRNAs. (A) RT-PCR analysis of CEP290 transcripts expressed in control (C3) and patient (P1 and P2) fibroblasts untreated or treated for 24 h with lipofectamine alone or associated to H36D antisense oligonucleotide. Images of agarose gel showing amplicons produced using primer pairs surrounding mutant exon 36. (B) Relative expression levels of full-length (black bars) and exon 36-skipped (grey bars) CEP290 mRNAs in control (C1-C3) and patient (P1 and P2) fibroblasts as determined by RT-qPCR. Bars show the mean±SEM from three independent experiments. C represents the pooled values of C1, C2 and C3. ****$p \leq 0.0001$, n.s., not significant.

Figure 8A:
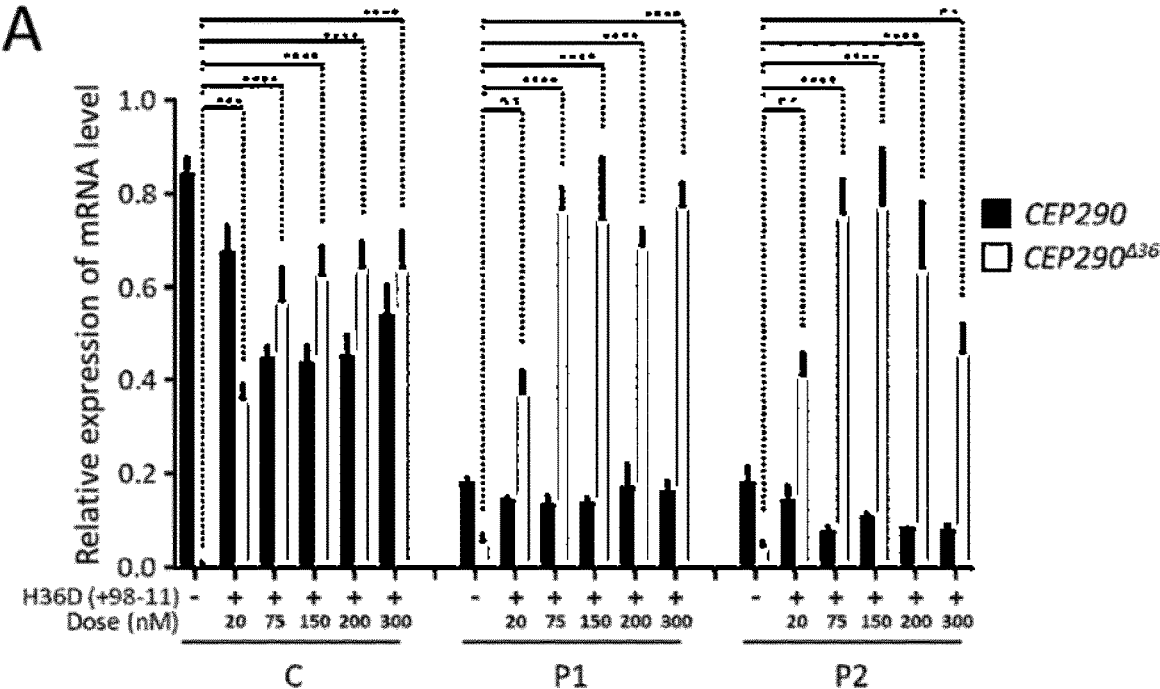
Figure 8B:
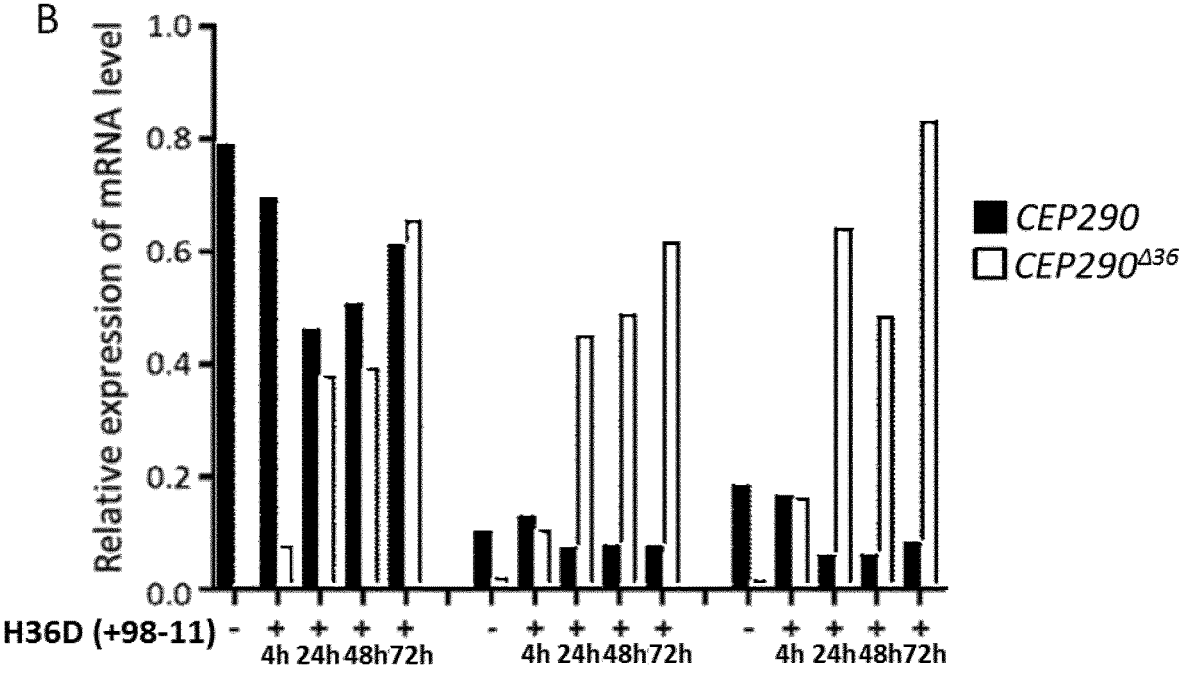
Figure 8C:
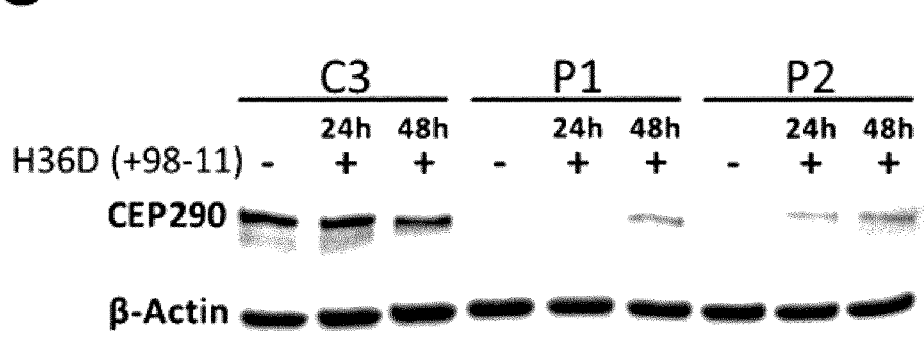

FIG. 8. Optimization of transfection conditions. (A) RT-qPCR analysis of reverse transcribed CEP290 mRNA extracted from control (C1-C3) and patient (P1 and P2) fibroblasts untreated or after transfection of increasing doses (20 nM to 300 nM) of H36D oligonucleotide. The graph shows the mean amounts (±SEM) of full-length (CEP290; black bars) and exon 36-skipped transcripts (CEP290Δ36; grey bars) from three independent experiments. C regroups the values obtained for C1, C2 and C3. *$p \leq 0.001$, **$p \leq 0.0001$, n.s., not significant. (B) RT-qPCR analysis of reverse transcribed CEP290 mRNA extracted from control (C1-C3) and patient (P1 and P2) fibroblasts untreated or treated during increasing times of treatment (4 h to 72 h) with 75 nM of H36D oligonucleotide. The graph shows the amounts of full-length (CEP290; black bars) and exon 36-skipped transcripts (CEP290Δ36; grey bars). C corresponds to C1, C2 and C3 pooled values. (C) CEP290 protein analysis in control (C3) and mutant (P1 and P2) cell lines untreated or treated with 75 nM of H36D during 24 h or 48 h. (D) Relative quantification of CEP290 protein abundance depending on treatment time. β-Actin was used for normalization.

FIG. 9: AON-treatment effect at protein level and impact on ciliation. (A) CEP290 protein analysis in control and mutant cell lines untreated or treated during 48 h with 75 nM of H36D. (B) Quantification of CEP290 protein abundance relative to β-Actin. Bars correspond to the mean value±SEM from three independent experiments=not significant.

A.U.=arbitrary unit. (C) Quantification of CEP290 immunofluorescence intensity at the basal body in each cell line. Each dot depicts the labeling intensity of the protein in individual cells recorded automatically from six microscope fields. The solid line indicates the mean. (D) Quantification of CP110 immunofluorescence intensity at centrosomes in quiescent fibroblasts. All automatic intensity measures were recorded from six fields. (E) Percentage of ciliated cells and (F) length of cilia axonemes in control and mutant fibroblasts. A minimum of 90 ciliated cells were considered for each cell lines. C corresponds to C1, C2 and C3 pooled values. *$p \leq 0.05$, *$p \leq 0.01$, *$p \leq 0.001$, **$p \leq 0.0001$, n.s=not significant, A.U.=arbitrary unit.

Figures 10, 11:
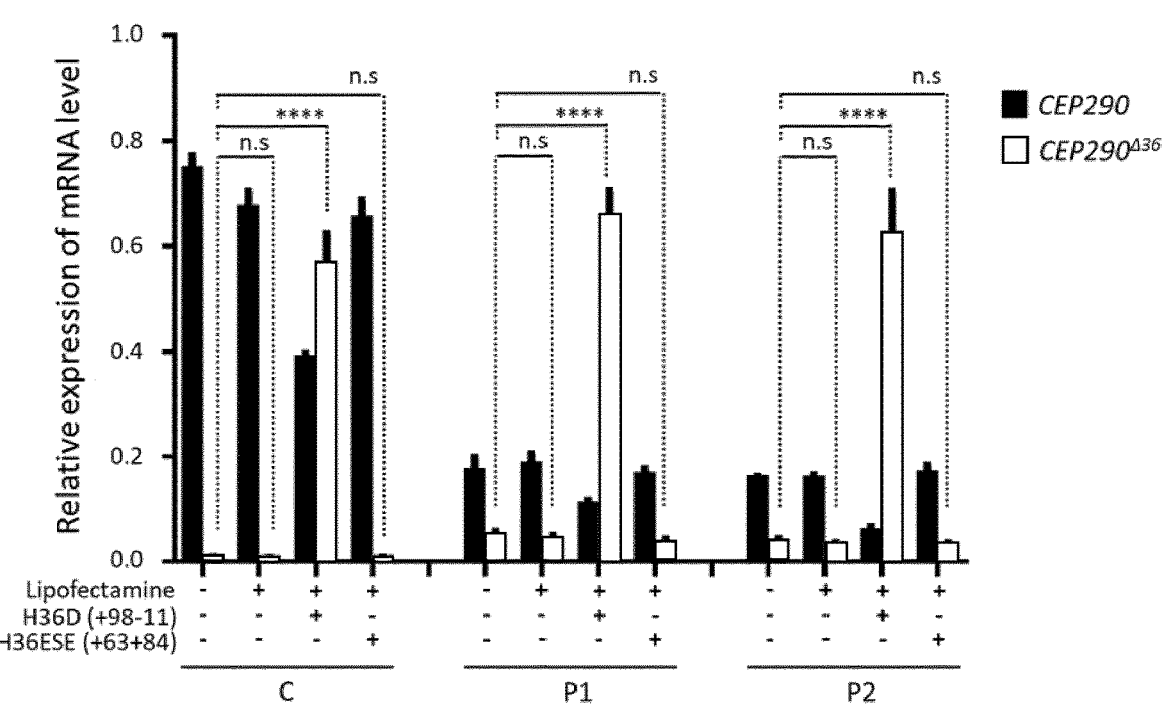

FIG. 10. Effect of AON-mediated exon 36 skipping on CEP290 mRNAs. Relative expression levels of full-length (black bars) and exon 36-skipped (grey bars) CEP290 mRNAs in control (C1-C3) and patient (P1 and P2) fibroblasts as determined by RT-qPCR. Bars show the mean±SEM from three independent experiments. C represents the pooled values of C1-C3. **** $p < 0.0001$, n.s., not significant.

FIG. 11. Biallelic exclusion of Cep290 exon 35 in Cep290$^{del/del}$ mice accounts for a milder retinal phenotype compared to that of compound heterozygous Cep290$^{ptc/del}$ mice. (A) Dark-adapted (scotopic; left graph) and light-adapted (photopic; right graph) ERG recordings in Cep290$^{del/del}$ and Cep290$^{ptc/del}$ compared to C57BL/6J mice at P30 ($N \geq 9$). (B) ONL thickness measured from control, Cep290$^{del/del}$ and Cep290$^{ptc/del}$ retinal sections shows a more severe reduction in Cep290$^{ptc/del}$ retinas compared to Cep2$^{del/del}$ counterparts at P30 (N=3). All data were statistically analysed using two-way ANOVA with post hoc Sidak's test and are shown as mean±SEM.

EXAMPLE 1

Material & Methods

Genetic Analysis

P1 and P2, two unrelated simplex cases born to apparently non-consanguineous parents originating from the transnational Flanders region were addressed to the Molecular Diagnosis Unit of our Genetic Department for molecular diagnosis of early-onset and severe retinal dystrophy. Patient DNAs were subjected to panel-based molecular testing of 199 genes involved in retinal dystrophies (Supplementary Material, FIG. S1) and variant datasets were filtered using the Polydiag software of the Polyweb series developed in-house. Biallelism for apparently homozygous CEP290 c.4723A>T variant was assessed by Sanger sequencing of parental DNA using primers specific to CEP290 exon 36 (Supplementary Material, Table S1). Written informed consents were obtained from all participating individuals and the study was approved by the Comite de Protection des Personnes "Ile-De-France II" (2015-03-03/DC 2014-2272).

In Silico Analysis of the Nonsense c.4723A>T (p.Lys1575*) Mutation on Splicing

The consequence of the c.4723A>T substitution on splicing was assessed using several prediction softwares, as previously described [21].

Cell Culture

Fibroblast cell lines were derived from skin biopsies of affected subjects (P1 and P2) and three healthy individuals (C1, C2 and C3). A table recapitulating their genetic and clinical features is presented in Supplementary Material, Table S2. Primary fibroblasts (<15 passages) were cultured as previously described [21].

AON and Transfection

Antisense oligonucleotides (AONs) specific to the donor splice site and ESE motifs of CEP290 exon 36 were identified using software prediction tools (m-fold and ESEfinder3.0 programs available online at http://mfold.r-na.albany.edu/ and http://rulai.cshl.edu/cgi-bin/tools/ESE3/esefinder.cgi respectively) and following general recommendations[23].

The position of H36D (+98–11) and H36ESE (+63+84) antisense oligonucleotide are represented in FIG. 6. The sequence of H36D was as following: 5'-UAGAAUC-UUACCCAAGCCGUUU-3' (SEQ ID NO: 1). The sequence of H36ESE was as following: 5'-UAGUGAAC-UAUCAGCCUGUAGU-3' (SEQ ID NO: 5).

Theses AONs were synthetized by Eurofins Genomics (St Quentin Fallavier, France) and contains 2'-O-methyl RNA and full-length phosphorothioate backbone. Cells at 80% confluence were transfected with different concentrations of AONs, ranging from 20-300 nmol/L, in Opti-MEM supplemented with 10% fetal bovine serum using Lipo-fectamine2000 (Invitrogen) according to the manufacturer's instruction. Cells were harvested for mRNA or protein analysis between 4 and 72 hours.

RNA Preparation and cDNA Synthesis

Total RNA was extracted using the RNeasy Mini Kit (Qiagen, Courtaboeuf, France) according to manufacturer's protocol. All samples were DNase-treated by the RNase-free DNase set (Qiagen). The concentration and purity of total RNA was determined using the Nanodrop-2000 spectropho-tometer (Thermo Scientific, Illkirch, France) before storage at −80° C. First-stranded cDNA synthesis was performed from 500 ng of total RNA extracted using the Verso cDNA kit (Thermo Scientific) with random hexamer anchored oligo(dT) primers at a 3:1 (vol:vol) ratio according to the manufacturer's instructions. A non-reverse transcription reaction (without enzyme; RT-) for one sample was prepared to serve as a control for reverse transcription PCR (RT-PCR) and real-time quantitative PCR (RT-qPCR) experiments.

RT-PCR

CEP290 splicing isoforms were amplified from reverse transcribed mRNAs (2 µl) in 20 µl of 1× Phusion HF buffer containing 4 mM dNTPs (Thermo Scientific), 0.4 units of Phusion High-Fidelity DNA polymerase (Thermo Scientific) and 10 µM of specific primer pairs (Supplementary Material, FIG. S1 and Table S1). No template (NTC) reactions were used as negative controls. PCRs were carried out on a 2720 Thermal Cycler (Applied Biosystems, Courtaboeuf, France) under the following conditions: initial denaturation at 98° C. for 5 min, followed by 30 cycles of 20 sec denaturation at 98° C., 15 sec annealing at 60° C. and 30 sec extension at 72° C. PCR products (5 µl) were separated by electropho-resis in a 3% low-melting agarose gel stained with ethidium bromide, visualized under UV lights and cut off. In-gel PCR products were further sequenced using the Big Dye Termi-natorCycle Sequencing Kit v3.1 (ABI Prism™, Applied Biosystems, Foster City, USA) on a 3500 automated sequencer (Applied Biosystems, Foster City, USA).

RT-qPCR Analysis

The abundance of CEP290 mRNA isoforms was mea-sured using primers specific to the unskipped (referred to as "full length") or skipped CEP290 versions. Primer sequences are listed in Supplementary Material, FIG. S1 and Table S2. GUSB (NM_000181.3) and RPLP0 (NM_001002.3) mRNAs were used to normalize the data. The cDNA (5 µl of a solution diluted at 1:25 in RNAse-free H2O) of each sample was subjected to PCR amplification in real-time in a buffer (20 µl) containing SYBR GREEN PCR Master Mix (Life Technologies) and 300 nM forward and reverse primers in the following conditions: activation of Taq polymerase and denaturation at 95° C. for 10 min followed by 50 cycles of 15 sec at 95° C., and 1min at 60° C. The specificity of the amplified products was determined after the analysis of the melting curve carried out at the end of each amplification using one cycle at 95° C. for 15 sec, then a graded thermal increase of 60° C. to 95° C. for 20 min. The data analysis and methodology were performed as previously described [8].

ProteinA Analysis

For Western blot analysis, total proteins from treated and untreated cells were extracted and quantified as described previously[21], and the relative abundance of CEP290 pro-tein was estimated by densitometry using β-Actin as refer-ence in each cell line.

For immunocytochemistry analysis, cells were grown for 24 hours on coverslips in 12-well plates to reach 90%-100% confluence and either transfected using the H36D (+98–11) AON or left untreated. After 24 hours, treated and untreated cells were serum-starved for 48 to 72 hours before cold methanol fixation and immune-labeling of ARL13B, CEP290, CP110, IFT88, pericentrin, RAB8A, γ-Tubulin and/or acetylated α-Tubulin. Immunofluorescence images were acquired and processed to analyze cilia abundance, axonemal length, subcellular localization and/or staining intensities. All experimental procedures and analytical meth-ods are described in Barny et al. 2018.

Immunocytochemistry Analysis

Cells were seeded on glass coverslips in a 12-well plate, 24 hours before transfection with the H36D (+98–11) AON, in the conditions described previously. Twenty-four hours after transfection, cells were incubated for 48 to 72 hours in serum-free medium. After serum-starvation, the cells were fixed with cold methanol (7 min at −20° C.) and washed twice with PBS. Untreated fibroblasts were processed in the same conditions. Cells were permeabilized and nonspecific sites were saturated in a PBS solution containing 3% bovine serum albumin and 0.5% TritonX-100 for 1 hour. Permea-bilized cells were incubated overnight at 4° C. with primary antibodies in PBS containing 3% bovine serum albumin and 0.1% TritonX-100: anti-Pericentrin rabbit antibody (1:1000, Abcam), anti-gamma-Tubulin mouse antibody (1:500, Sigma-Aldrich), anti-CEP290 rabbit antibody (1:100, Novus Biologicals), anti-CP110 rabbit antibody (1:100, Protein-Tech), anti-acetylated α-Tubulin mouse antibody (1:1000; Sigma-Aldrich), anti-ARL13B rabbit antibody (1:200, Pro-teinTech), anti-IFT88 rabbit antibody (1:100, ProteinTech) and anti-RAB8A mouse antibody (1:50, Abnova). After three washes in PBS, the cells were incubated for 1 hour at room temperature with secondary antibodies in PBS solution containing 3% bovine serum albumin and 0.1% TritonX-100: anti-rabbit IgG goat antibody coupled to Alexa-Fluor 488 and anti-mouse IgG goat antibody coupled to Alexa-Fluor 568 (1:1000; Life Technologies). After three additional washes with PBS, the coverslips were mounted on slides using a mounting medium containing DAPI (ProLong Gold antifade reagent with DAPI, Invitrogen) to stain the cell nuclei Immunofluorescence images were obtained using a Zeiss spinning disk microscope. Exposure times and settings for image processing were constant for all samples to allow sample comparison. The number of Z-stacks collected was variable between the samples but optimized for capturing maximum fluorescent signals. Deconvoluted images were projected into one picture using ImageJ software Z-project tool with the maximum intensity setting. The total fluorescence contained in 16 μm2 squares centered on the centrosome as determined by gamma-Tubulin staining was recorded to measure the intensity of CEP290 and CP110 labelling in the peri-centrosomal region. Integrated pixel densities were quantified in each square using ImageJ software. The final images were generated using ImageJ software.

Statistics

All statistical analyses were run using Prism6 software, and the significance was determined using one-way ANOVA with post hoc Tukey's test. The data obtained from C1, C2 and C3 were systematically pooled for immune-labelling analysis. Error bars reflect the SEM.

Results

Panel-Based Molecular Diagnosis Testing Identifies Homozygosity for the CEP290 c.4723A>T Founder Mutation in Two Individuals with Congenital Retinal Dystrophy of Variable Severity We studied two apparently unrelated non-consanguineous sporadic cases of Belgian and/or French Flanders origin addressed for congenital retinal dystrophy with no extraocular involvement. The first individual (P1) presented at birth with nystagmus, photoaversion, hyperopia (+6 diopters LRE), absent cone-derived electroretinogram but present, yet highly hypovolted, rod-derived responses. He experienced spontaneous improvement of his visual capacities in the first decade of life. At the age of 20 years, he displayed a tubular visual field with a visual acuity (VA) of 20/67 (RE) and 20/50 (LE) and thin retinal vessels, optic nerve atrophy and peripheral pigmentary deposits at the fundus. While the initial symptoms suggested early-onset severe cone-rod dystrophy, this outcome is consistent with a rod-dominant LCA-like disease referred to as early-onset severe rod-cone dystrophy. The second individual (P2) presented with a typical LCA10-associated disease, i.e. a stationary congenital blindness with nystagmus, inability to follow lights or objects and flat cone- and rod-derived electroretinographic responses. Panel-based molecular diagnosis for inherited retinal dystrophies (190 genes) and Sanger-based familial segregation analysis identified homozygosity for the Flanders founder CEP290 c.4723A>T (p.Lys1575*) mutation in the two cases.

In Silico Analysis Suggests that the CEP290 c.4723A>T Mutation Induced Nonsense-Associated Altered Splicing We analyzed the effect of the c.4723A>T mutation on splicing by using prediction software solutions scrutinizing splice signals and ESS/ESE binding sites. The substitution of an adenine by a thymine (mutation) or a guanine but not a cytosine at position c.4723 is predicted to increase exon 36 ESS/ESE ratio, thus increasing the susceptibility of skipping compared to the wild-type sequence (Table 2).

TABLE 2

Impact of mutations on ESS and ESE motifs.

| | | EX_SKIP predictions | | | HOT-SKIP predictions | | | Skipping predictions of mutant allele |
| | Nucleotide | ESS | ESE | ESS/ESE | ESS | ESE | ESS/ESE | compared to WT allele |
|---|---|---|---|---|---|---|---|---|
| c.4723 | A | 12 | 88 | 0.14 | 2 | 17 | 0.12 | — |
| (exon 36) | T | 19 | 75 | 0.25 | 9 | 4 | 2.25 | Higher chance |
| | G | 13 | 87 | 0.15 | 3 | 16 | 0.19 | Higher chance |
| | C | 11 | 82 | 0.13 | 1 | 11 | 0.09 | Lower chance |

Effect of nucleotide change at position c.4723 on ESS and ESE motifs according to EX-SKIP and HOT-SKIP prediction programs. The WT and mutant alleles identified in this study are labeled in blue and red, respectively. ESS=Exonic splicing silencer; ESE=Exonic splicing enhancer.

mRNA Analysis Supports c.4723A>T-Mediated Nonsense-Associated Altered Splicing and Basal Endogenous Alternative Splicing of Exon 36

Figure 2A:
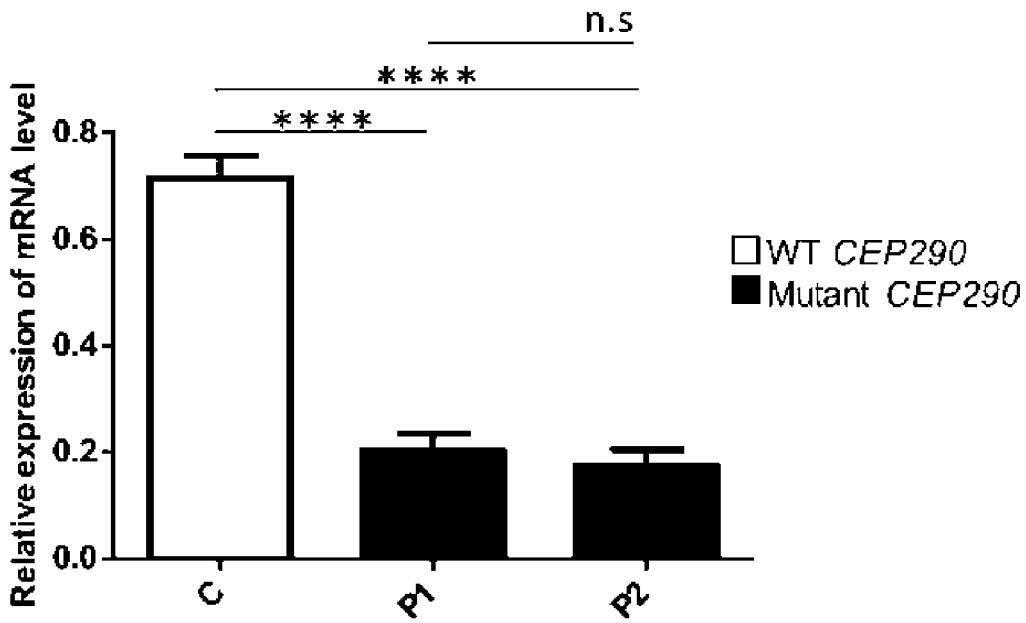
Figure 2B:
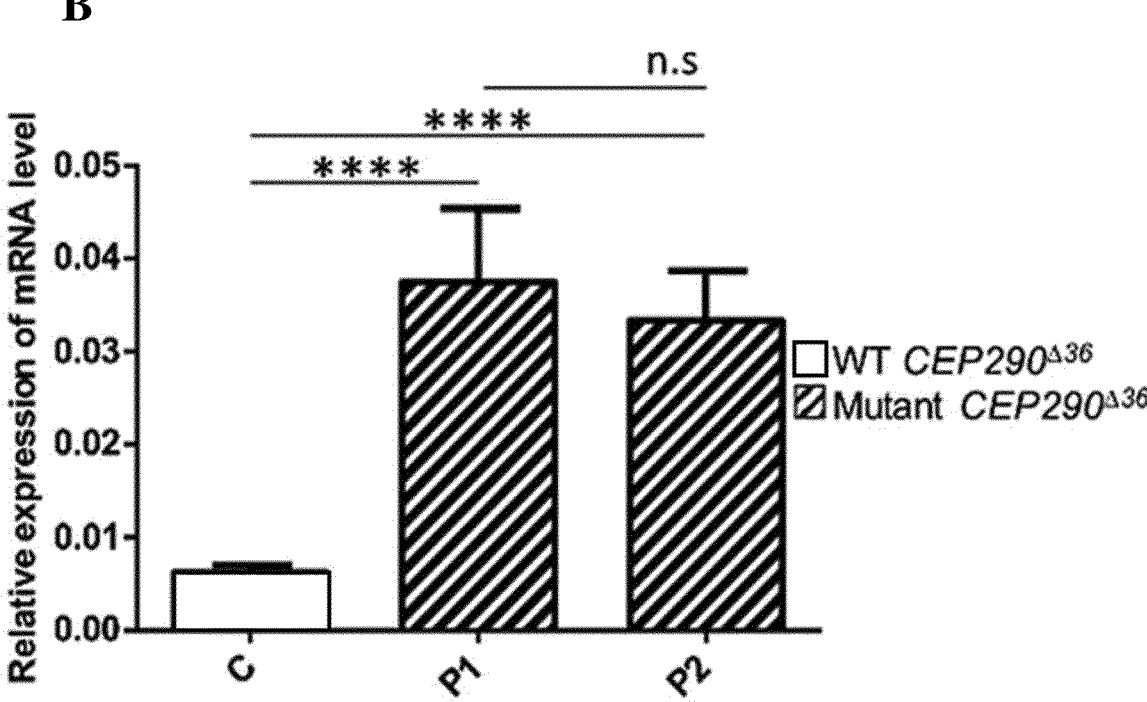

Agarose gel analysis and Sanger sequencing of RT-PCR products generated from P1 and P2 skin fibroblast mRNAs carrying the c.4723A>T variant in homozygosity using primers specific to CEP290 exons 35 and 37 (tables not shown) detected the full-length mutant cDNA (CEP290) and a PTC-free alternatively spliced product lacking exon 36 (CEP290Δ36). Control fibroblasts expressed the full-length wild-type cDNA but the CEP290Δ36 product was undetectable, contrasting with human retina where both isoforms were identified. These observations indicate that CEP290 exon 36 undergoes endogenous basal skipping in the retina and that, consistent with in silico analysis, the c.4723A>T variant induces nonsense-associated altered splicing (data not shown). Interestingly, RT-qPCR analysis using primers specific to the CEP290Δ36 isoform (tables not shown) detected the product in control fibroblasts (FIG. 2B). This observation supports some contribution of endogenous basal exon skipping in CEP290-frame-restoration documented in P1 and P2 mutant fibroblasts. RT-qPCR analysis using primers specific to the full-length mutant/wild-type cDNA (tables not shown) showed reduced abundance of the mutant product in P1 and P2 cell lines compared to the wild-type counterpart in controls supporting nonsense-mediated RNA decay (NMD) of the mRNA carrying the nonsense c.4723A>T variant (FIG. 2A).

Protein Analysis Detects Low Levels of a CEP290 Protein that Localizes at the Centrosome in Patient Fibroblasts Homozygous for the c.4723A>T Nonsense Mutation Western Blot analysis of protein extracts from serum-starved P1 and P2 fibroblasts detected minimal amounts of a CEP290 product around 290 KDa (FIGS. 3 and 4) that localized at the centrosome upon immunocytochemistry analysis (FIG. 4). These results indicate that the PTC-free alternatively spliced product lacking exon 36 is translated into a stable protein that can be recruited at the centrosome as does the wild-type protein.

Cilia Analysis of Serum-Starved Patient Fibroblasts Shows Apparently Normal RAB8A Localization at the Centrosome but Elongated Axonemes CEP290 exon 36 encodes 36 amino-acids contributing to the CEP290 domain that binds RAB8A, the recruitment of which at the centrosome leads to the release of the cilia formation-suppressor CP110, hence initiating ciliogenesis during transition of the cells from proliferation to quiescence [24-26]. Interestingly, RAB8A immune-labeling in quiescent fibroblasts showed comparable localization at the basal body in patient and control fibroblasts, suggesting that the absence of information encoded by exon 36 does not alter the recruitment of RAB8A at the centrosome (FIG. 6). Furthermore, we observed comparable CP110 abundance at the centrosome of control and P1 fibroblasts indicating correct release upon RAB8A recruitment (FIG. 6A). In contrast, the amount of CP110 at the centrosome of P2 cells was significantly higher than in control and P1 cells (p≤0.0001; FIG. 6A). CP110 accumulation in P2 could be correlated to reduced abundance of CEP290Δ36aa protein compared to P1. Consistent with normal and impaired CP110 release, cilia abundance was in the normal range and reduced in P1 and P2 fibroblasts, respectively (p≤0.001; FIG. 5B).

Figure 6C:
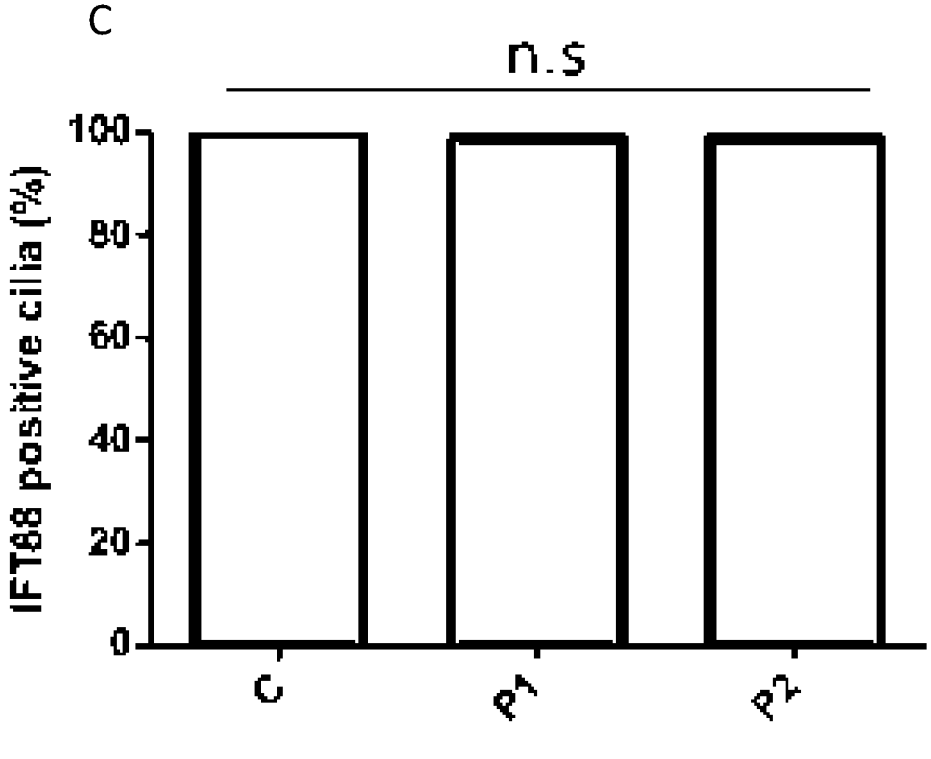

On another note, measuring cilia length, we observed statistically significant axonemal elongation in both patient cell lines compared to controls (mean axonemal sizes of 4.4 μm in P1 and 4.9 μm in P2 versus 3.9 μm in controls, p≤0.0001; FIG. 6C). Cilia in P2 expressing lower amounts of the CEP290Δ36aa isoform at the centrosome displayed significantly longer axoneme than P1 counterparts (p≤0.01; FIG. 6C), further supporting a correlation between the severity of cilia phenotype and the amount of minimally shortened CEP290 cells are able to produce from mutant alleles.

As observed in controls cells, IFT88 immune-labelling in patient fibroblasts revealed this IFT complex B protein all along the axoneme (FIG. 6C), assuming that the abnormal cilia elongation in patient cells is not related to a defect of the anterograde trafficking driven by IFT88.

Targeting the Consensus Donor Splice Site Enables Dose- and Time-Dependent Skipping of CEP290 Exon 36

Figure 7B:
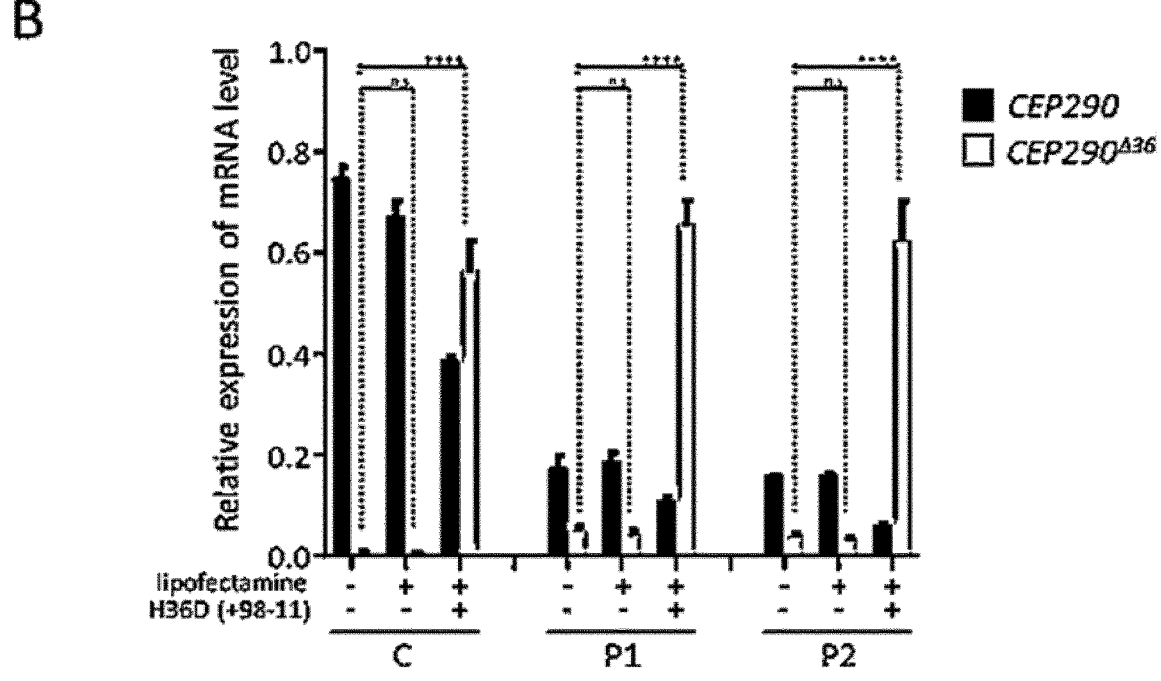

The RNA conformation around CEP290 exon 36 and splicing regulatory elements were predicted in silico using m-fold and ESEfinder3.0 programs to design splice switching AON. We designed 2'-O-methyl-phosphorothioate (2'-OMePs) AONs targeting either the donor site (H36D (+98−11)) (FIG. 1). The AONs was delivered in patient and control fibroblasts at a final concentration of 150 nM for 24 h prior to mRNA analysis. Treatment with H36D (+98−11) AON elevated significantly the abundance of products lacking exon 36 and reduced by half the amount of full-length mutant and wild-type products in patient and control fibroblasts, respectively (FIG. 7). Due to NMD, the abundance of the full-length mutant was significantly reduced in patient compared to control cells (FIG. 7B). Consistent with a switch from a mRNA prone to NMD to a PTC-free isoform, the abundance of the alternatively spliced product lacking exon 36 in patient fibroblasts was comparable to that of controls upon treatment with the H36D (+98−11) AON. Treatment with the transfection reagent alone did not alter CEP290 expression whatever the cell line.

To assess dose-dependent skipping efficiency, patient and control fibroblasts were treated with increasing doses of H36D (+98−11) AON for 24 h, revealing that the amount of alternatively splice products lacking exon 36 reached a maximum in almost all cell lines at an AON concentration of 75 nmol/l (FIG. 8A). At this concentration, we observed accumulation of alternatively splice products and CEP290 proteins with treatment time (FIGS. 8B, C and D).

The RNA conformation around CEP290 exon 36 and splicing regulatory elements were predicted in silico using m-fold and ESEfinder3.0 programs to design splice switching AONs. We designed 2'-O-methyl-phosphorothioate (2'-OMePs) AONs targeting the donor site (H36D (+98−11)) and an exonic splicing enhancer region (H36ESE (+63+84)). The AONs were delivered in patient and control fibroblasts at a final concentration of 150 nM and the transfected cell were maintained in culture for 24 h prior to mRNA analysis. While treatment with H36ESE (+63+84) had no effect on the relative abundance of transcripts lacking exon 36, transfection with H36D (+98−11) AON resulted in a statistically significant elevation of the abundance of products lacking exon 36 and reduction by half of the amount of full-length mutant and wild-type products in patient and control fibroblasts, respectively (FIG. 10). Due to NMD, the abundance of the full-length mutant was significantly reduced in patient compared to control cells (FIG. 10). Consistent with a switch from a mRNA prone to NMD to a PTC-free isoform, the abundance of the alternatively spliced product lacking exon 36 in patient fibroblasts was comparable to that of controls upon treatment with the H36D (+98–11) AON. Treatment with the transfection reagent alone did not alter CEP290 expression whatever the cell line (FIG. 10).

Figure 9C:
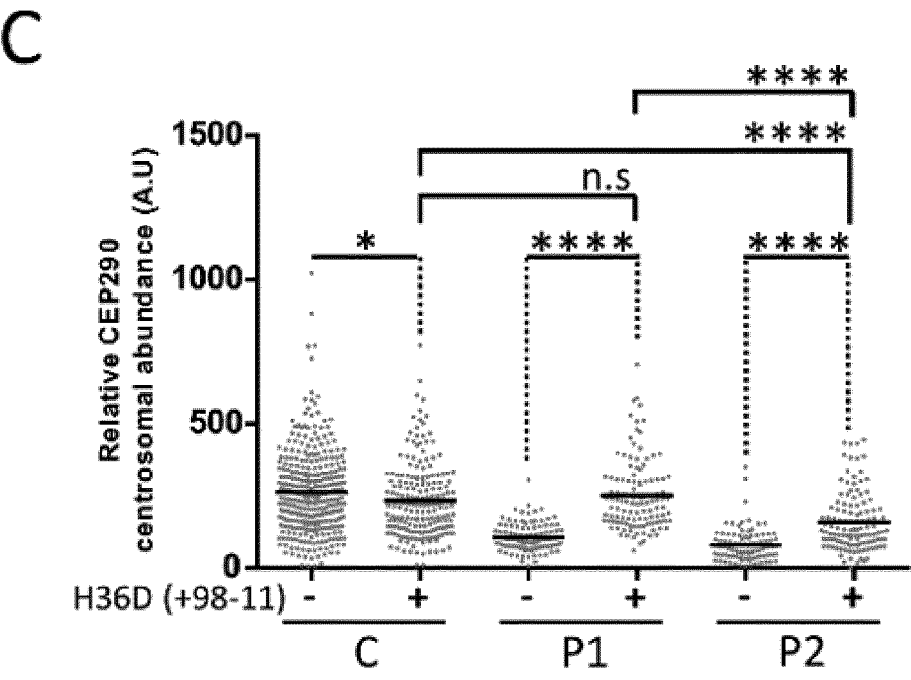
Figure 9D:
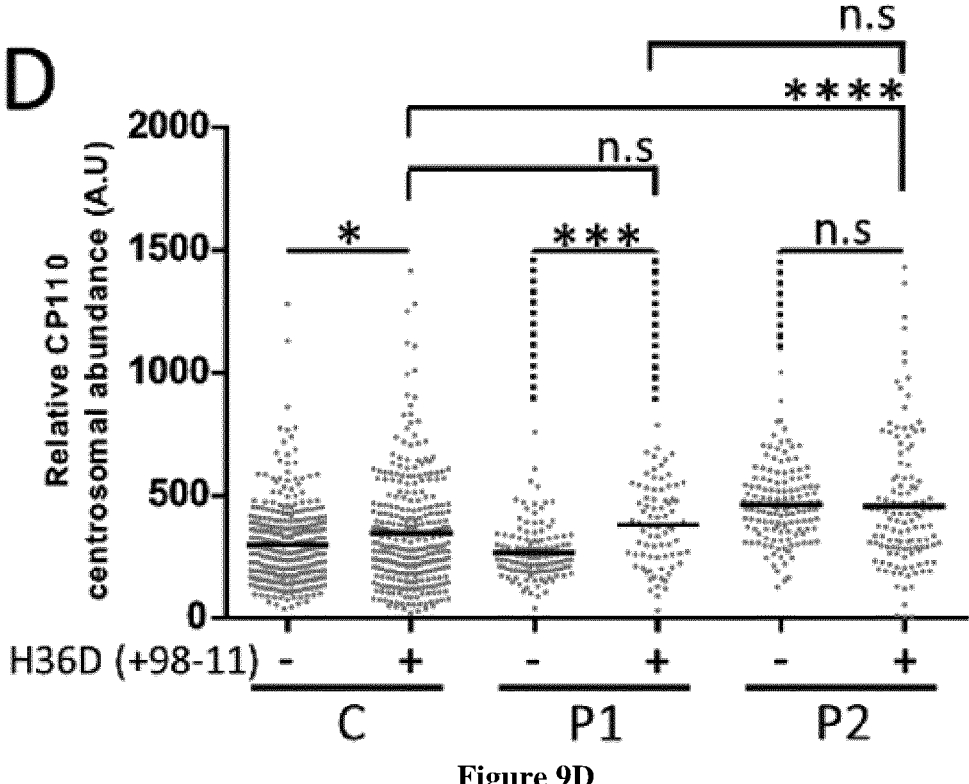
Figure 9E:
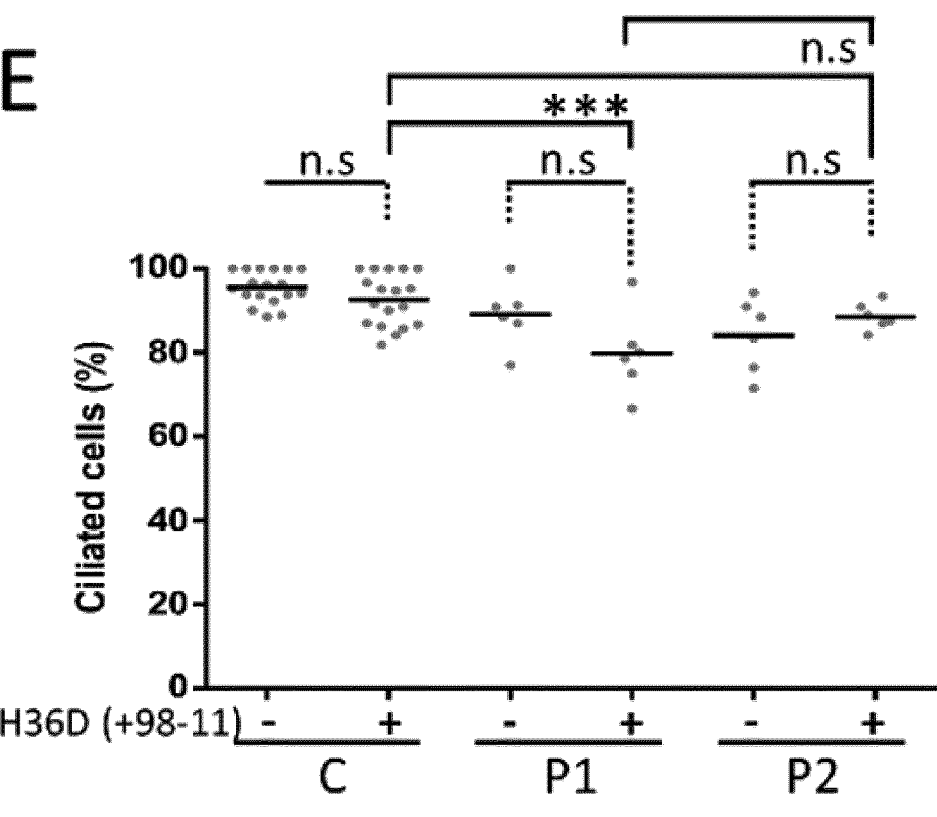
Figure 9F:
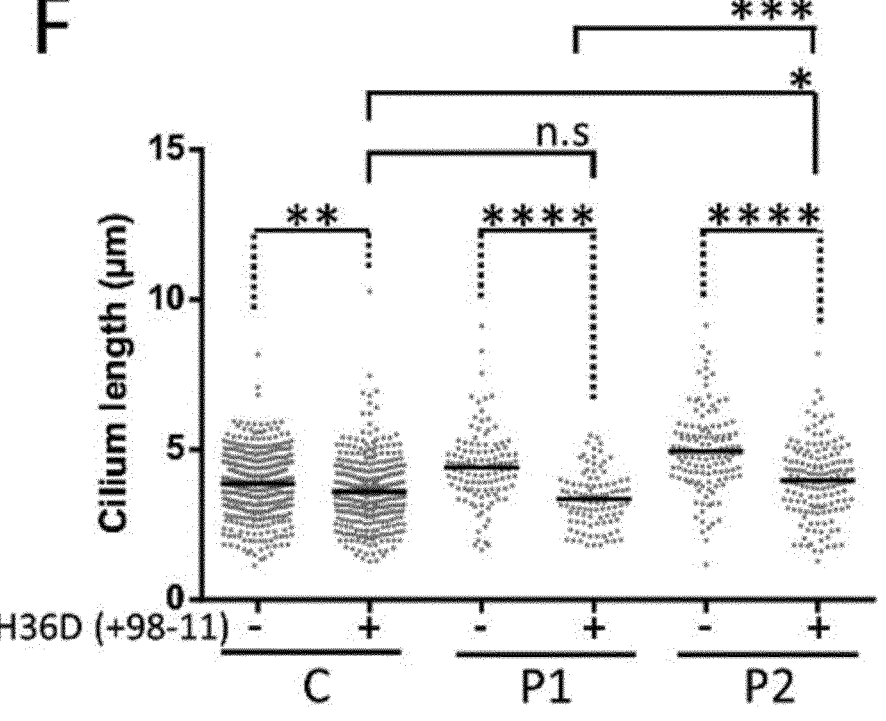

AON-Mediated Skipping Allows to Bypass Protein-Truncation but may not Restore Full CEP290 Functions The abundance of full length CEP290 mRNA in control cells treated with 75 nM of H36D (+98–11) AON for 48 h was ca. 60% that of untreated control cells, as determined by RT-qPCR (FIG. 8B), indicating that ca. 40% of full length CEP290 pre-mRNA underwent AON-mediated skipping of exon 36. The amount of CEP290 protein (full-length+ $\Delta$36aa) was comparable in treated and untreated cells (FIGS. 9A and B), suggesting that the CEP290$\Delta$36aa isoform is stable. Yet, treated cells displayed a moderate diminution of CEP290 staining at the centrosome (p≤0.05, FIG. 9C) with statistically significant, yet minimal, alteration of CP110 centrosomal staining (p≤0.05, FIG. 9D). The abundance of ciliated cells tended to be slightly diminished (95.5% versus 92.5%, FIG. 9F) as was the mean axonemal length (3.9 µm versus 3.6 µm, p≤0.01, FIG. 9E). Together, these results suggest that the CEP290$\Delta$36aa isoform interferes with the wild-type counterpart and can compromise ciliation, possibly through disorganization of centriolar satellites. The same treatment in P1 cells, allowed a highly significant increase in CEP290$\Delta$36aa protein abundance, as determined by Western Blot and immunocytochemistry analyses (FIGS. 9A, B and C). Interestingly, the intensity of CEP290 staining at the centrosome reached that of treated control cells (FIG. 9C). However, expressing increased levels of CEP290$\Delta$36aa isoform in cells deprived of wild-type CEP290 altered the dynamics of centriolar satellites, as documented by increased dispersion of CP110-specific centrosomal staining (p≤0.001, FIG. 9D). Consistently, the proportion of ciliated cells tended to diminish (89% versus 79.8%) upon AON treatment (FIG. 9F), as did axonemal length (4.4 µm versus 3.5 µm, p≤0.0001, FIG. 9E).

In summary, here we report expression of a PTC-free CEP290 mRNA resulting from endogenous and selective exclusion of exon 36 encompassing the founder CEP290 c.4723A>T nonsense mutation in two apparently unrelated individuals. We show that a CEP290 isoform is produced that localizes to centrosomes and that cilia are produced upon serum starvation, yet improperly, as demonstrated by significant axonemal elongation.

EXAMPLE 2

Previously, we demonstrated that targeting the donor splice site of CEP290 exon 36 using 2'OMePS antisense splice-switching oligonucleotide can improve cilia metabolism in fibroblasts derived from patients homozygous for the c.4723A>T (p.1575X, exon 36) mutation. Furthermore, we made proof of concept of AON-mediated skipping of the orthologous exon in the mouse (exon 35) using the intravitreal delivery route in WT C57BL/6J mice (46). To assess the therapeutic potential of intravitreal injections of our previously reported m35ESE AON (46), we generated a mouse model carrying an endogenous deletion of exon 35 in homozygosity (Cep290del/del) and a mouse line carrying the deletion in compound heterozygosity with a premature termination codon (Cep290del/PTC). Here, we report retinal degeneration in both Cep290del/del and Cep290del/PTC mouse lines.

Material & Methods

Generation of Cep290 Murine Models

Two Cep290 murine models were generated by using a CRISPR/Cas9 system at the Imagine institute. Guide RNAs (sgRNAs) were designed via the CRISPOR (http://crispor-.tefor.net/) to introduce a premature termination codon (PTC) in coding exon 35 of the Cep290 gene and to skip this exon (del35), respectively. C57BL/6J 4-weeks old female mice were superovulated by intraperitoneal injection of 5 IU PMSG (SYNCRO-PART® PMSG 600 UI, Ceva) followed by 5 UI hCG (Chorulon 1500 UI, Intervet) at an interval of 46 h-48 h and mated with C57BL/6J male mice. The next day, zygotes were collected from the oviducts and exposed to hyaluronidase (H3884, Sigma-Aldrich) to remove the cumulus cells and then placed in M2 medium (M7167, Sigma-Aldrich) into a CO2 incubator (5% CO2, 37° C.). SgRNAs were hybridized with cas9 (WT) protein and injected into the pronucleus of the C57Bl/6J zygotes. Surviving zygotes were placed in KSOM medium (MR-106-D, Merck-Millipore) and cultured overnight to two-cell stage and then transferred into the oviduct of B6CBAF1 pseudopregnant females. Mice carrying either mutations were selected by genotyping of genomic DNA using by Sanger sequencing specific primers flanking exon 35. Heterozygous mice were backcrossed with C57BL/6J mice to remove potential off-targets and the offspring was mated to obtain animals displaying exon 35 deletion in homozygosity (Cep290del/del) and in compound heterozygosity with the PTC (Cep290del/PTC), respectively. Cep290del/del and Cep290del/PTC mice were bred and maintained in the LEAT Facility of Imagine Institute under a 12 hours dark/light cycle prior to electrophysiological and histological analysis at postnatal (P) days 30, 60 and 120 (P30, P60 and P120) and 18, 21 and 30 (P18, P21, P30), respectively. Wild-type C57BL/6J mice of same ages were used as controls in all analyses. All animal procedures were performed in compliance with guidelines for animal experiments in France and conducted in accordance with the ethical principles.

Electroretinography

Electroretinograms (ERGs) were recorded using the Celeris™ ERG for rodents (Diagnosys LLC, Cambridge, UK). Briefly, mice were dark-adapted overnight and anesthetized by intramuscular injection of ketamine 120 mg/kg and xylazine 16 mg/kg. Pupils were dilated with a drop of 0.5% tropicamide and a drop of 10% phenylephrine before applying sterile ophthalmic gel on the corneal surface to ensure electrical contact and maintain corneal integrity. Animals were maintained on the Celeris™ warming support for the entire ERG procedure to maintain the body temperature at 38° C. Stimuli and recordings were generated with the Celeris™ electrode stimulators; a ground electrode was inserted subcutaneously. The dark-adapted ERG protocol consisted of four steps with increasing stimuli strengths from 0.01 to 3 cd.s/m2. Light-adapted ERGs were recorded after light adaptation for 8 minutes. The photopic recordings consisted of 2 steps with increasing stimuli from 3 to 10 cd.s/m2. The statistical analysis was run using Prism6 software and the significance of the difference in a-wave amplitudes between Cep290 mice models and same age wild-type C57BL/6J mice was determined using two-way ANOVA with post hoc Sidak's test.

Histology

Mice were euthanized by cervical dislocation. The eyes were enucleated and immediately fixed for 12 hours in a phosphate buffered saline (PBS) solution containing 4% paraformaldehyde. At the histology platform of Imagine institute, the eyecups were dehydrated in serial gradients of ethanol using an automated tissue processor (ASP300S, Leica), and embedded in paraffin before microtome sectioning (2×HM 340E, Microm France). Six-microns serial sections were cut longitudinally and stained with haematoxylin and eosin. Each slide was scanned using a commercial imaging system (NanoZoomer S210, Hamamatsu) and analysed using the NDPview software. The thickness of the outer nuclear layer was plotted versus the distance (0.25, 0.5, 0.75, 1, 1.25, 1.5, 1.75, 2 and 2.25 mm) from the optic nerve (ON). Three mice from each group were included in this analysis. The ONL thickness of Cep290 mice models was compared with that of same age wild-type C57BL/6J mice by ANOVA with post hoc Sidak's test (Prism 6.0 software, San Diego, CA).

Results

The CRISPR-Cas9 technology proved efficient to introduce a premature termination codon in the murine Cep290 exon 35 (c.4749del, p.His1583Glnfs6*) and to delete the complete exon, respectively. Only very few Cep290PTC/PTC pups were born to Cep290PTC/+×Cep290PTC/+ matings and animals displayed developmental delay, ataxia, hydrocephalus, cerebellar development defects, cystic kidneys, severe retinal degeneration and did not survived beyond P45 (data not shown). In contrast, Cep290PTC/+× Cep290del/+ matings gave birth to Cep290+/+, Cep290+/ del, Cep290PTC/+ and Cep290del/PTC animals which were viable and developed normally. ERG responses of Cep290del/del photoreceptors were diminished from the age of P30 and completely absent by P120 (FIG. 11A). Histological analysis at P30 showed a moderate reduction of the thickness of the outer nuclear layer (ONL; photoreceptors nuclei) compared to wild-type Cep290+l+retina (FIG. 11B). The ONL thickness was significantly decreased by P60 and reduced to 1-2 layers of nuclei by P120 (FIG. 11B). The retinal degeneration in Cep290del/PTC animals occurred earlier and progressed more rapidly. At P14 (eye opening), ERG responses of both rods and cones photoreceptors from Cep290del/PTC mice were significantly reduced (FIG. 11A). The histological structure appeared normal at this age but the ONL thickness decreased very rapidly with eye opening and it was reduced to only one row of nuclei at P30 (FIG. 11B).

CONCLUSIONS

In human individuals, homozygosity and compound heterozygosity for truncating mutations in the 35th coding exon (exon 36) of the CEP290 gene, including the founder c.4723A>T variant, cause a congenital or early-onset and severe non-syndromic retinal degeneration (LCA10 and EOSRD, respectively). However, in the mouse, our results show that homozygosity for a truncating mutation in the orthologous exon (c.4749del; Cep290PTC/PTC) cause a very severe ciliopathy phenotype reminiscent of Meckel syndrome type 4 (MKS4). In contrast, mice homozygous for the deletion of exon 35 which does not alter the reading frame displayed a moderate and isolated retinal phenotype, supporting the view that the CEP290 isoform lacking residues encoded by exon 35 maintains some function. Interestingly, mice carrying the deletion in compound heterozygosity with the c.4749del had an intermediate phenotype consisting in severe retinal disease reminiscent of LCA with moderate extraocular anomalies. While the onset and severity of multiorgan lesions in Cep290PTC/PTC hampers manipulating splicing in vivo, the Cep290del/PTC model is ideally suited to assess whether AON-mediated skipping of exon 35 carrying the c.4749del can slowdown the retinal degeneration from a LCA-like disease to an Cep290del/del EOSRD phenotype (FIG. 11).

REFERENCES

Throughout this application, various references describe the state of the art to which this invention pertains. The disclosures of these references are hereby incorporated by reference into the present disclosure.

Kaplan, J. Leber Congenital Amaurosis: From Darkness to Spotlight. Ophthalmic Genetics 2008, 29, 92-98.

2. Hanein, S. et al. Leber congenital amaurosis: Comprehensive survey of the genetic heterogeneity, refinement of the clinical definition, and genotype—phenotype correlations as a strategy for molecular diagnosis. Human Mutation 2004, 23, 306-317.

3. Craige, B. et al. CEP290 tethers flagellar transition zone microtubules to the membrane and regulates flagellar protein content. J. Cell Biol. 2010, 190, 927-940.

4. den Hollander, A. I., Roepman, R., Koenekoop, R. K. & Cremers, F. P. M. Leber congenital amaurosis: genes, proteins and disease mechanisms. Prog Retin Eye Res 2008, 27, 391-419.

5. Perrault, I. et al. Spectrum of NPHP6/CEP290 mutations in Leber congenital amaurosis and delineation of the associated phenotype. Hum. Mutat. 2007, 28, 416.

6. Cideciyan, A. V. et al. Centrosomal-ciliary gene CEP290/ NPHP6 mutations result in blindness with unexpected sparing of photoreceptors and visual brain: implications for therapy of Leber congenital amaurosis. Human Mutation 2007, 28, 1074-1083.

7. Preising, M. N. et al. [The Phenotypic Spectrum of Ophthalmic Changes in CEP290 Mutations]. Klin Monbl Augenheilkd 2019, 236, 244-252.

8. Gerard, X. et al. AON-mediated Exon Skipping Restores Ciliation in Fibroblasts Harboring the Common Leber Congenital Amaurosis CEP290 Mutation. Mol Ther Nucleic Acids 2012, 1, e29.

9. Collin, R. W. et al. Antisense Oligonucleotide (AON)-based Therapy for Leber Congenital Amaurosis Caused by a Frequent Mutation in CEP290. Mol Ther Nucleic Acids 2012, 1, e14.

10. Parfitt, D. A. et al. Identification and Correction of Mechanisms Underlying Inherited Blindness in Human iPSC-Derived Optic Cups. Cell Stem Cell 2016, 18, 769-781.

11. Dulla, K. et al. Splice-Modulating Oligonucleotide QR-110 Restores CEP290 mRNA and Function in Human c 2991+1655A>G LCA10 Models. Mol Ther Nucleic Acids 2018, 12, 730-740.

12. Garanto, A. et al. In vitro and in vivo rescue of aberrant splicing in CEP290-associated LCA by antisense oligonucleotide delivery. Hum Mol Genet 2016, 25, 2552-2563.

13. Bainbridge, J. W. B. et al. Effect of Gene Therapy on Visual Function in Leber's Congenital Amaurosis. http:// dx.doi.org.gate2.inist.fr/10.1056/NEJMoa0802268 2009. doi:10.1056/NEJMoa0802268

14. Hauswirth, W. W. et al. Treatment of Leber Congenital Amaurosis Due to RPE65 Mutations by Ocular Subretinal Injection of Adeno-Associated Virus Gene Vector: Short-Term Results of a Phase I Trial. Hum Gene Ther 2008, 19, 979-990.

15. Maguire, A. M. et al. Safety and Efficacy of Gene Transfer for Leber's Congenital Amaurosis. N Engl J Med 2008, 358, 2240-2248.

16. Seo, S. et al. Subretinal Gene Therapy of Mice With Bardet-Biedl Syndrome Type 1. Invest. Ophthalmol. Vis. Sci. 2013, 54, 6118-6132.

17. Kloeckener-Gruissem, B. et al. Novel VCAN mutations and evidence for unbalanced alternative splicing in the pathogenesis of Wagner syndrome. Eur J Hum Genet 2013, 21, 352-356.

18. Papon, J. F. et al. Abnormal respiratory cilia in non-syndromic Leber congenital amaurosis with CEP290 mutations. J. Med. Genet. 2010, 47, 829-834.

19. Drivas, T. G., Wojno, A. P., Tucker, B. A., Stone, E. M. & Bennett, J. Basal exon skipping and genetic pleiotropy: A predictive model of disease pathogenesis. Sci Transl Med 2015, 7, 291ra97.

20. Barny, I. et al. Basal exon skipping and nonsense-associated altered splicing allows bypassing complete CEP290 loss-of-function in individuals with unusually mild retinal disease. Hum. Mol. Genet. 2018. doi: 10.1093/hmg/ddy179

21. Littink, K. W. et al. A novel nonsense mutation in CEP290 induces exon skipping and leads to a relatively mild retinal phenotype. Invest. Ophthalmol. Vis. Sci. 2010, 51, 3646-3652.

22. Roosing, S. et al. A Rare Form of Retinal Dystrophy Caused by Hypomorphic Nonsense Mutations in CEP290. Genes (Basel) 2017, 8.

23. Disterer, P. et al. Development of Therapeutic Splice-Switching Oligonucleotides. Hum Gene Ther 2014, 25, 587-598.

24. Tsang, W. Y. et al. CP110 suppresses primary cilia formation through its interaction with CEP290, a protein deficient in human ciliary disease. Dev. Cell 2008, 15, 187-197.

25. Kim, J., Krishnaswami, S. R. & Gleeson, J. G. CEP290 interacts with the centriolar satellite component PCM-1 and is required for Rabb localization to the primary cilium. Hum. Mol. Genet. 2008, 17, 3796-3805.

26. Stowe, T. R., Wilkinson, C. J., Iqbal, A. & Stearns, T. The centriolar satellite proteins Cep72 and Cep290 interact and are required for recruitment of BBS proteins to the cilium. Mol. Biol. Cell 2012, 23, 3322-3335.

27. Ramsbottom, S. A. et al. Targeted exon skipping of a CEP290 mutation rescues Joubert syndrome phenotypes in vitro and in a murine model. Proc Natl Acad Sci USA 2018, 115, 12489-12494.

28. Drivas, T. G., Holzbaur, E. L. F. & Bennett, J. Disruption of CEP290 microtubule/membrane-binding domains causes retinal degeneration. J Clin Invest 2013, 123, 4525-4539.

29. Rachel, R. A. et al. CEP290 alleles in mice disrupt tissue-specific cilia biogenesis and recapitulate features of syndromic ciliopathies. Hum. Mol. Genet. 2015, 24, 3775-3791.

30. Chang, B. et al. In-frame deletion in a novel centrosomal/ciliary protein CEP290/NPHP6 perturbs its interaction with RPGR and results in early-onset retinal degeneration in the rd16 mouse. Hum. Mol. Genet. 2006, 15, 1847-1857.

31. Shimada, H. et al. In Vitro Modeling Using Ciliopathy-Patient-Derived Cells Reveals Distinct Cilia Dysfunctions Caused by CEP290 Mutations. Cell Rep 2017, 20, 384-396.

32. Barny, I. et al. Description of two siblings with apparently severe CEP290 mutations and unusually mild retinal disease unrelated to basal exon skipping or nonsense-associated altered splicing. Adv Exp Med Biol (under review)

33. Valentine, C. R. The association of nonsense codons with exon skipping. Mutat. Res. 1998, 411, 87-117.

34. Cartegni, L., Chew, S. L. & Krainer, A. R. Listening to silence and understanding nonsense: exonic mutations that affect splicing. Nat. Rev. Genet. 2002, 3, 285-298.

35. Shiga, N. et al. Disruption of the splicing enhancer sequence within exon 27 of the dystrophin gene by a nonsense mutation induces partial skipping of the exon and is responsible for Becker muscular dystrophy. J. Clin. Invest. 1997, 100, 2204-2210.

36. Mokrzan, E. M., Lewis, J. S. & Mykytyn, K. Differences in Renal Tubule Primary Cilia Length in a Mouse Model of Bardet-Biedl Syndrome. NEE 2007, 106, e88-e96.

37. Smith, L. A. et al. Development of Polycystic Kidney Disease in Juvenile Cystic Kidney Mice: Insights into Pathogenesis, Ciliary Abnormalities, and Common Features with Human Disease. JASN 17, 2821-2831 (2006).

38. Sohara, E. et al. Nek8 Regulates the Expression and Localization of Polycystin-1 and Polycystin-2. J Am Soc Nephrol 2008, 19, 469-476.

39. Tammachote, R. et al. Ciliary and centrosomal defects associated with mutation and depletion of the Meckel syndrome genes MKS1 and MKS3. Hum Mol Genet 2009, 18, 3311-3323.

40. He, M. et al. The Kinesin-4 Protein KIF7 Regulates Mammalian Hedgehog Signaling by Organizing the Cilia Tip Compartment. Nat Cell Biol 2014, 16, 663-672.

41. Sanders, A. A. W. M. et al. KIAA0556 is a novel ciliary basal body component mutated in Joubert syndrome. Genome Biol 2015, 16.

42. Stayner, C. et al. An ovine hepatorenal fibrocystic model of a Meckel-like syndrome associated with dysmorphic primary cilia and TMEM67 mutations. Sci Rep 2017, 7.

43. Srivastava, S. et al. A human patient-derived cellular model of Joubert syndrome reveals ciliary defects which can be rescued with targeted therapies. Hum Mol Genet 2017, 26, 4657-4667.

44. Garanto, A. et al. Unexpected CEP290 mRNA Splicing in a Humanized Knock-In Mouse Model for Leber Congenital Amaurosis. PLoS One 2013, 8.

45. Marshall, W. F., Qin, H., Brenni, M. R. & Rosenbaum, J. L. Flagellar Length Control System: Testing a Simple Model Based on Intraflagellar Transport and Turnover. Mol Biol Cell 2005, 16, 270-278.

46. Gerard, X. et al. Intravitreal injection of Splice-switching oligonucleotides to manipulate splicing in retinal cells. Mol Ther Nucleic Acids, 2015, 1; 4e250.

The invention claimed is:

1. An antisense oligonucleotide consisting of a sequence set forth as SEQ ID NO: 1.

2. A method for performing antisense oligonucleotide-mediated exon skipping in a subject in need thereof comprising delivering to target cells of the subject an amount of an antisense oligonucleotide, wherein the subject suffers from a retinal dystrophy caused by a mutation which modifies the splicing and/or creates a premature termination by a nonsense mutation in exon 36 of the CEP290 gene, or a frameshift mutation in exon 36 of the CEP290 gene, wherein said antisense oligonucleotide is complementary to a nucleic acid sequence of the CEP290 gene selected from the group consisting of the ESE sequences of said exon 36 and a sequence comprising the donor splice site around the exon 36/intron 36 boundary, and the antisense oligonucleotide performs antisense oligonucleotide-mediated exon skipping in the pre-mRNA from the CEP290 gene which mutation causes the retinal dystrophies in the target cells of the subject.

3. The method according to claim 2, wherein the subject suffers from a retinal dystrophy caused by at least one mutation selected from the group consisting of: c.4723A>T, c.4771C>T, c.4714G>T, c.4786_4790del, c.4791_4794del, c.4732G>T, c.4625_4626insCATG (35), c.4792_4795del, c.4801C>T, c.4805C>T, and c.4811G>A.

4. The method of claim 2, wherein the retinal dystrophy is selected from the group consisting of Leber congenital amaurosis and other early-onset severe retinal dystrophies (LCA-like), rod-cone dystrophies (retinitis pigmentosa), cone-rod dystrophies, macular dystrophies including age-related macular degeneration, any ciliopathy involving the retina including Joubert syndrome, Senior-Loken syndrome, Bardet-Biedel syndrome, Meckel and Meckel-like syndromes, Refsum syndrome, Stargardt disease, Usher syndrome, hereditary optic neuropathies congenital stationary night blindness, dyschromatopsia and achromatopsia.

5. A method for restoring the function of CEP290 in a cell carrying a nonsense mutation in exon 36 of the CEP290 gene, or a frameshift mutation in exon 36, in a subject harbouring said mutation, comprising delivering to the subject an antisense oligonucleotide consisting of a sequence complementary to a nucleic acid sequence of the CEP290 gene that is necessary to alter splicing and excludes the exon encoding the premature termination codon inserted into CEP290 mRNA by a nonsense mutation in exon 36 or a frameshift mutation in exon 36 or an upstream exon, wherein the nucleic acid sequence of the CEP290 gene is selected from the group consisting of the exon splicing enhancer (ESE) sequences of said mutant exon 36 and a sequence comprising the donor splice site of CEP290 exon 36.

6. The method according to claim 5, wherein said cell carrying at least one mutation selected from the group consisting of: c.4723A>T, c.4771C>T, c.4714G>T, c.4786_4790del, c.4791_4794del, c.4732G>T, c.4625_4626insCATG (35), c.4792_4795del, c.4801C>T, c.4805C>T, and c.4811G>A.

7. A method of treating a retinal dystrophy in a subject harbouring a nonsense mutation, located in exon 36 of the CEP290 gene or a frameshift mutation in exon 36 of the CEP290 gene or an upstream exon resulting in the apparition of a premature termination codon in exon 36, leading to a truncated protein, wherein said method comprises the step of modulating the splicing of the exon 36 which contains a nonsense mutation or a premature termination codon generated by a frameshift mutation within the same exon wherein said method is carried out by exposing CEP290 pre-mRNA to an antisense oligonucleotide (AONs) which is complementary to the exon splicing enhancer (ESE) sequences of said mutant exon 36 and a sequence comprising the donor splice site of CEP290 exon 36.

8. The method according to claim 7 wherein, said subject harbours at least one mutation selected from the group consisting of: c.4723A>T, c.4771C>T, c.4714G>T, c.4786_4790del, c.4791_4794del, c.4732G>T, c.4625_4626insCATG (35), c.4792_4795del, c.4801C>T, c.4805C>T, and c.4811G>A.

9. The method according to claim 2, wherein the antisense oligonucleotide is complementary to a sequence comprising the donor splice site of CEP290 exon 36.

10. The method according to claim 2, wherein the antisense oligonucleotide comprises a nucleic acid sequence set forth as SEQ ID NO: 1.

11. The method according to claim 2, wherein the antisense oligonucleotide consisting of a nucleic acid sequence set forth as SEQ ID NO: 1.

12. A method of treating a retinal dystrophy comprising delivering a pharmaceutical composition containing antisense oligonucleotide alone or in association with a vector, to a subject harbouring a nonsense mutation or a premature termination codon in exon 36 generated by a frameshift mutation within the same or an upstream exon mutation in the CEP290 gene, wherein the antisense oligonucleotide consists of a sequence complementary to a nucleic acid sequence of CEP290 gene that is necessary to alter splicing and exclude the exon encoding the premature termination codon inserted into the CEP290 mRNA by a nonsense mutation in exon 36 or a frameshift mutation in exon 36 or an upstream exon, and wherein said nucleic acid sequence of CEP290 gene is selected from the group consisting of the exon splicing enhancer (ESE) sequences of said mutant exon 36 and a sequence comprising the donor splice site of CEP290 exon 36.

13. The antisense oligonucleotide of claim 1, which is complementary to a nucleic acid sequence of CEP290 pre-mRNA, wherein the antisense oligonucleotide targeting the donor splice site (H36D), is capable of altering splicing by blocking the recognition of exon 36 and allows bypassing protein truncation associated with any mutation introducing a premature termination codon in exon 36, while maintaining the open reading frame, and leads to the production of near full-length CEP290 protein.

14. The method according to claim 2, wherein the antisense oligonucleotide is selected from the group consisting of oligodeoxyribonucleotides, oligoribonucleotides, Locked Nucleic Acid (LNA) oligonucleotides, morpholinos oligonucleotides, tricyclo-DNA-antisense oligonucleotides, U7- or U1-mediated antisense oligonucleotides, peptide-conjugated, nanoparticle-complexed antisense oligonucleotides, 2'-O-Me RNA/ENA chimera oligonucleotides, and 2'-O-methyl-phosphorothioate oligonucleotides.

15. The method according to claim 5, wherein the antisense oligonucleotide is complementary to a sequence comprising the donor splice site of CEP290 exon 36.

16. The method according to claim 5, wherein the antisense oligonucleotide comprises a nucleic acid sequence set forth as SEQ ID NO: 1.

17. The method according to claim 5, wherein the antisense oligonucleotide consisting of a nucleic acid sequence set forth as SEQ ID NO: 1.

18. The method according to claim 7, wherein the antisense oligonucleotide is complementary to a sequence comprising the donor splice site of CEP290 exon 36.

19. The method according to claim 7, wherein the antisense oligonucleotide comprises a nucleic acid sequence set forth as SEQ ID NO: 1.

20. The method according to claim 7, wherein the antisense oligonucleotide consisting of a nucleic acid sequence set forth as SEQ ID NO: 1.

21. The method according to claim 5, wherein the antisense oligonucleotide is selected from the group consisting of oligodeoxyribonucleotides, oligoribonucleotides, Locked Nucleic Acid (LNA) oligonucleotides, morpholinos oligonucleotides, tricyclo-DNA-antisense oligonucleotides, U7- or U1-mediated antisense oligonucleotides, peptide-conjugated, nanoparticle-complexed antisense oligonucleotides, 2'-O-Me RNA/ENA chimera oligonucleotides, and 2'-O-methyl-phosphorothioate oligonucleotides.

22. The method according to claim 7, wherein the antisense oligonucleotide is selected from the group consisting of oligodeoxyribonucleotides, oligoribonucleotides, Locked Nucleic Acid (LNA) oligonucleotides, morpholinos oligonucleotides, tricyclo-DNA-antisense oligonucleotides, U7- or U1-mediated antisense oligonucleotides, peptide-conjugated, nanoparticle-complexed antisense oligonucleotides, 2'-O-Me RNA/ENA chimera oligonucleotides, and 2'-O-methyl-phosphorothioate oligonucleotides.

* * * * *

SEQUENCE LISTING

<160> NUMBER OF SEQ ID NOS: 6

<210> SEQ ID NO 1
<211> LENGTH: 22
<212> TYPE: RNA

-continued

<213> ORGANISM: Artificial
<220> FEATURE:
<223> OTHER INFORMATION: Synthetic H36D (+98-11) RNA

<400> SEQUENCE: 1
uagaaucuua cccaagccgu uu                                                          22

<210> SEQ ID NO 2
<211> LENGTH: 22
<212> TYPE: RNA
<213> ORGANISM: Artificial
<220> FEATURE:
<223> OTHER INFORMATION: Synthetic H_sense RNA

<400> SEQUENCE: 2
acuacaggcu gauaguucac ua                                                          22

<210> SEQ ID NO 3
<211> LENGTH: 22
<212> TYPE: DNA
<213> ORGANISM: Artificial
<220> FEATURE:
<223> OTHER INFORMATION: Synthetic H36D(+98-11) DNA

<400> SEQUENCE: 3
tagaatctta cccaagccgt tt                                                          22

<210> SEQ ID NO 4
<211> LENGTH: 22
<212> TYPE: DNA
<213> ORGANISM: Artificial
<220> FEATURE:
<223> OTHER INFORMATION: Synthetic H_sense DNA

<400> SEQUENCE: 4
actacaggct gatagttcac ta                                                          22

<210> SEQ ID NO 5
<211> LENGTH: 22
<212> TYPE: RNA
<213> ORGANISM: Artificial
<220> FEATURE:
<223> OTHER INFORMATION: Synthetic H36ESE (+63+84) RNA

<400> SEQUENCE: 5
uagugaacua ucagccugua gu                                                          22

<210> SEQ ID NO 6
<211> LENGTH: 22
<212> TYPE: DNA
<213> ORGANISM: Artificial
<220> FEATURE:
<223> OTHER INFORMATION: Synthetic H36ESE (+63+84) DNA

<400> SEQUENCE: 6
tagtgaacta tcagcctgta gt                                                          22